(12) United States Patent
Höglinger et al.

(10) Patent No.: US 10,369,123 B2
(45) Date of Patent: Aug. 6, 2019

(54) PERK ACTIVATOR FOR THE TREATMENT OF NEURODEGENERATIVE DISEASES

(71) Applicants: DEUTSCHES ZENTRUM FÜR NEURODEGENERATIVE ERKRANKUNGEN E.V. (DZNE), Bonn (DE); Klinikum Rechts Der Isar Technische Universität München, München (DE); Günter Höglinger, Langenhagen (DE); Julius Bruch, Bonn (DE); Thomas Rösler, München (DE)

(72) Inventors: Günter Höglinger, Langenhagen (DE); Julius Bruch, Bonn (DE); Thomas Rösler, München (DE)

(73) Assignees: Deutsches Zentrum für Neurodegenerative Erkrankungen E.V. (DZNE), Bonn (DE); Klinikum Rechts Der Isar Technische Universität München, München (DE)

( * ) Notice: Subject to any disclaimer, the term of this patent is extended or adjusted under 35 U.S.C. 154(b) by 0 days.

(21) Appl. No.: 15/503,636

(22) PCT Filed: Aug. 14, 2015

(86) PCT No.: PCT/EP2015/068734
§ 371 (c)(1),
(2) Date: Feb. 13, 2017

(87) PCT Pub. No.: WO2016/024010
PCT Pub. Date: Feb. 18, 2016

(65) Prior Publication Data
US 2017/0304241 A1    Oct. 26, 2017

(30) Foreign Application Priority Data
Aug. 14, 2014  (EP) .................................. 14181071

(51) Int. Cl.
| | |
|---|---|
| *A61K 31/195* | (2006.01) |
| *A61K 31/415* | (2006.01) |
| *A61K 31/4152* | (2006.01) |
| *A61K 31/42* | (2006.01) |
| *A61K 31/4709* | (2006.01) |
| *A61K 31/4704* | (2006.01) |
| *A61K 31/00* | (2006.01) |

(52) U.S. Cl.
CPC .......... *A61K 31/195* (2013.01); *A61K 31/415* (2013.01); *A61K 31/4152* (2013.01); *A61K 31/42* (2013.01); *A61K 31/4704* (2013.01); *A61K 31/4709* (2013.01); *A61K 31/00* (2013.01)

(58) Field of Classification Search
None
See application file for complete search history.

(56) References Cited

FOREIGN PATENT DOCUMENTS

WO    2013/192165 A2    12/2013

OTHER PUBLICATIONS

Bruch, et al.; "PERK activation mitigates tau pathology in vitro and in vivo;" EMBO Molecular Medicine; 14 pages; published online: Feb. 1, 2017.
Stockwell, et al.; "Mechanism-Based Screen for G1/S Checkpoint Activators Identifies a Selective Activator of EIF2AK3/PERK Signalling;" PLOS ONE; 7(1): e28568; 16 pages.
EIF2AK3 Activator, CCT020312—Calbiochem; downloaded on Apr. 19, 2018 from: http://www.emdmillipore.com/US/en/product/EIF2AK3-Activator-CCT020312-Calbiochem,EMD_BIO-324879.
Axten et al.; "Discovery of 7-Methyl-5-(1-{[3-(trifluoromethyl)phenyl]acetyl}-2,3-dihydro-1H-indol-5-yl)-7H-pyrrolo[2,3-d]pyrimidin-4-amine (GSK2606414), a Potent and Selective First-in-Class Inhibitor of Protein Kinase R (PKR)-like Endoplasmic Reticulum Kinase (PERK);" J. Med. Chem.; 2012, 55, pp. 7193-7207.
B'chir et al.; "The eIF2α/ATF4 pathway is essential for stress-induced autophagy gene expression;" Nucleic Acids Research, 2013, vol. 41, No. 16, pp. 7683-7699 (Published online on Jun. 26, 2013).
Boxer et al.; "Davunetide in patients with progressive supranuclear palsy: a randomised, double-blind, placebo-controlled phase 2/3 trial;" Lancet Neurol 2014; www.thelancet.com/neurology, 10 pages, http://dx.doi.org/10.1016/S1474-4422(14)70088-2 (Published online on May 27, 2014 ).

(Continued)

*Primary Examiner* — Kamal A Saeed
(74) *Attorney, Agent, or Firm* — Mayer Brown LLP

(57) ABSTRACT

The present invention relates to a novel method for the treatment and/or prophylaxis of a tau-mediated neurodegenerative disease and/or of a tau-mediated neurodegenerative pathological condition, especially of a neurodegenerative disease and/or of a neurodegenerative pathological condition associated with and/or accompanied by tau aggregation, and in particular for the treatment and/or prophylaxis of a tauopathy; compounds and/or agents and compositions for such treatment and/or prophylaxis, and the manufacture of the compounds and/or agents and compositions suitable for the said treatment and/or prophylaxis. In this regard, the present invention relates especially to the use of compounds acting as PERK activator, a prodrug thereof, a derivative thereof and/or a pharmaceutically acceptable salt of any thereof, as a medicament. In contrast to the prior art which addresses mainly PERK inhibition, or occasionally only the apoptotic arm of PERK of activation, the present invention pertains to the effects of indirect or direct PERK activation achieved via the neuroprotective arm of PERK signaling.

14 Claims, 10 Drawing Sheets
Specification includes a Sequence Listing.

(56) References Cited

OTHER PUBLICATIONS

Bruch et al.; "Early Neurodegeneration in the Brain of a Child Without Functional PKR-like Endoplasmic Reticulum Kinase;" J Neuropathol Exp Neurol; vol. 74, No. 8, Aug. 2015, pp. 850-857.

Cullinan et al.; "Nrf2 Is a Direct PERK Substrate and Effector of PERK-Dependent Cell Survival;" Molecular and Cellular Biology, Oct. 2003, vol. 23, No. 20, pp. 7198-7209.

Escobar-Khondiker et al.; "Annonacin, a Natural Mitochondrial Complex I Inhibitor, Causes Tau Pathology in Cultured Neurons;" The Journal of Neuroscience, Jul. 18, 2007, 27(29), pp. 7827-7837.

Gani et al.; "Tauroursodeoxycholic acid prevents stress induced aggregation of proteins in vitro and promotes PERK activation in HepG2 cells;" Archives of Biochemistry and Biophysics, 568 (2015), pp. 8-15 (Available online on Jan. 8, 2015).

Hetz et al.; "Disturbance of endoplasmic reticulum proteostasis in neurodegenerative diseases," Nature Reviews | Neuroscience, vol. 15, Apr. 2014, pp. 233-249 (Published online on Mar. 12, 2014).

Höglinger et al.; "Identification of common variants influencing risk of the tauopathy progressive supranuclear palsy;" Nature Genetics, vol. 43, No. 7, Jul. 2011, pp. 699-707 (published online on Jun. 19, 2011).

Lee et al.; "Activation of PERK Signaling Attenuates Aβ-Mediated ER Stress," PLoS ONE 5(5): e10489, May 5, 2010, doi:10.1371/journal.pone.0010489 (8 pages).

Loewen et al.; "The Unfolded Protein Response Protects from Tau Neurotoxicity In Vivo," PLoS ONE 5(9): e13084, Sep. 29, 2010, doi:10.1371/journal.pone.0013084 (6 pages).

Ma et al., "Suppression of eIF2α kinases alleviates Alzheimer's disease-related plasticity and memory deficits," Nature Neuroscience, vol. 16, No. 9, Sep. 2013, pp. 1299-1307 (published online on Aug. 11, 2013).

Moon et al., "Autophagy and Protein Kinase RNA-Like Endoplasmic Reticulum Kinase (PERK)/Eukaryotic Initiation Factor 2 Alpha Kinase (eIF2α) Pathway Protect Ovarian Cancer Cells From Metformin-Induced Apoptosis," Molecular Carcinogenesis, 2016, 55, pp. 346-356 (Published online on Feb. 7, 2015).

Moreno et al., "Oral Treatment Targeting the Unfolded Protein Response Prevents Neurodegeneration and Clinical Disease in Prion-Infected Mice," www.ScienceTranslationalMedicine.org, Oct. 9, 2013, vol. 5, Issue 206, 206ra138 (11 pages).

Nijholt et al., "The unfolded protein response is associated with early tau pathology in the hippocampus of tauopathies," J Pathol, 2012; 226, pp. 693-702.

Ozasa et al., "The Antipsychotic Olanzapine Induces Apoptosis in Insulin-secreting Pancreatic β Cells by Blocking PERK-mediated Translational Attenuation," Cell Structure and Function, 2013, 38, pp. 183-195 (Published online on Jun. 28, 2013).

Pytel et al., "Enzymatic Characterization of ER Stress-Dependent Kinase, PERK, and Development of a High-Throughput Assay for Identification of PERK Inhibitors," Journal of Biomolecular Screening, 2014, vol. 19(7), pp. 1024-1034 (published online on Mar. 5, 2014).

Scheper et al., "The unfolded protein response in neurodegenerative diseases: a neuropathological perspective," Acta Neuropathol, 2015, 130, pp. 315-331 (Published online on Jul. 26, 2015).

Scheper et al., "A New PERKspective on Neurodegeneration," www.ScienceTranslationalMedicine.org, Oct. 9, 2013, vol. 5, Issue 206, 206fs37, 3 pages.

Stockwell et al., "Mechanism-Based Screen for G1/S Checkpoint Activators Identifies a Selective Activator of EIF2AK3/PERK Signalling," PLoS ONE, Jan. 12, 2012, 7(1): e28568. doi:10.1371/journal.pone.0028568 (16 pages).

Stutzbach et al., "The unfolded protein response is activated in disease-affected brain regions in progressive supranuclear palsy and Alzheimer's disease," Acta Neuropathologica Communications, 2013, 1:31 (13 pages).

Tolosa et al., "A Phase 2 Trial of the GSK-3 Inhibitor Tideglusib in Progressive Supranuclear Palsy," Movement Disorders, 2014, vol. 29, No. 4, pp. 470-478 (Published online on Feb. 14, 2014).

Vaccaro et al., "Pharmacological reduction of ER stress protects against TDP-43 neuronal toxicity in vivo," Neurobiology of Disease, 2013, 55, pp. 64-75 (Available online on Apr. 5, 2013).

Van der Harg et al., "The unfolded protein response mediates reversible tau phosphorylation induced by metabolic stress," Cell Death and Disease, 2014, 5, e1393, 9 pages; doi:10.1038/cddis.2014.354 (published online on Aug. 28, 2014).

Wu et al., "Salvianolic acid B protects human endothelial cells from oxidative stress damage: a possible protective role of glucose-regulated protein 78 induction," Cardiovascular Research, 2009, 81, pp. 148-158 (online publish-ahead-of-print on Sep. 24, 2008).

Xie et al., "Identification and Characterization of PERK Activators by Phenotypic Screening and Their Effects on NRF2 Activation," PLoS ONE, Mar. 17, 2015, 10(3): e0119738 (21 pages) doi:10.1371/journal.pone.0119738.

Xu et al., "Memory deficits correlate with tau and spine pathology in P301S MAPT transgenic mice," Neuropathology and Applied Neurobiology, 2014, 40, 833-843 (Published online Article Accepted on May 28, 2014).

Yan et al., "Resveratrol-induced cytotoxicity in human Burkitt's lymphoma cells is coupled to the unfolded protein response," BMC Cancer, 2010, 10:445 (10 pages).

Yang et al., "Phenformin Activates the Unfolded Protein Response in an AMP-activated Protein Kinase (AMPK)-dependent Manner," The Journal of Biological Chemistry, May 10, 2013, vol. 288, No. 19, pp. 13631-13638 (published online on Apr. 2, 2013).

Zhu et al., "Eif-2a Protects Brainstem Motoneurons in a Murine Model of Sleep Apnea," The Journal of Neuroscience, Feb. 27, 2008, 28(9), pp. 2168-2178.

Bouman et al., "Parkin is transcriptionally regulated by ATF4: evidence for an interconnection between mitochondrial stress and ER stress," Cell Death and Differentiation, 2011, 18, pp. 769-782 (published online on Nov. 26, 2010).

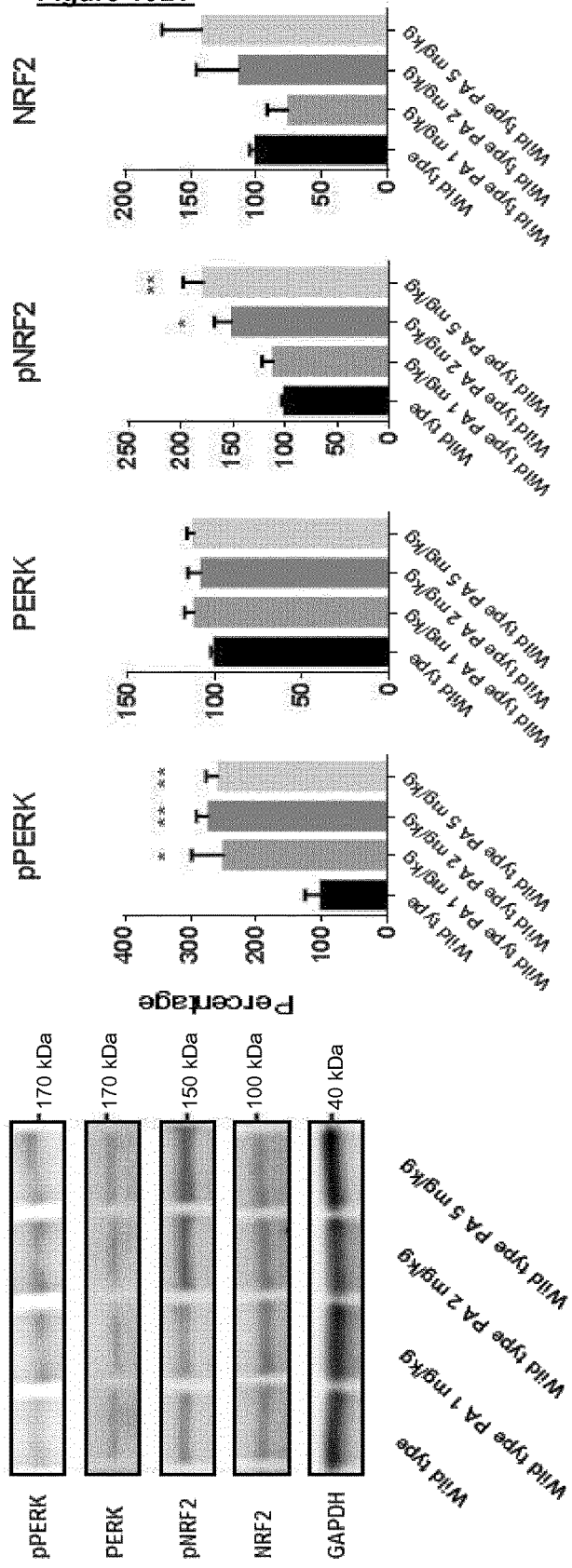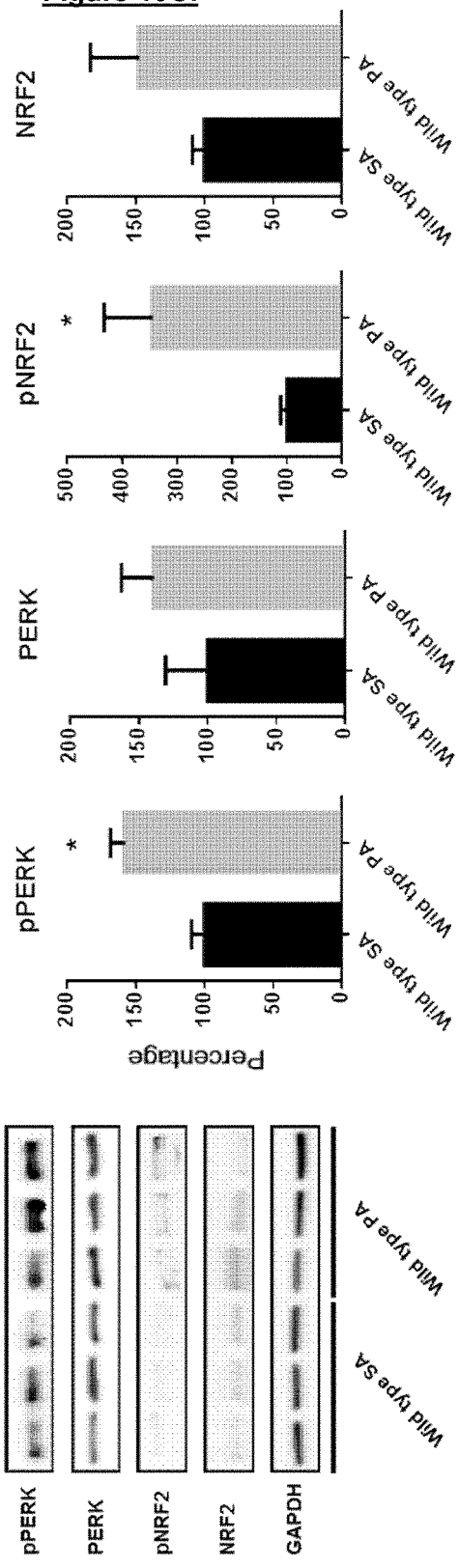
Figure 10B:
Figure 10C:

SEQUENCE LISTING

<160> NUMBER OF SEQ ID NOS: 6

<210> SEQ ID NO 1
<211> LENGTH: 32
<212> TYPE: DNA
<213> ORGANISM: human
<220> FEATURE:
<221> NAME/KEY: misc_feature
<223> OTHER INFORMATION: Forward Primer pRK172/htau39

<400> SEQUENCE: 1
gatctctaga atcacaaacc ctgcttggcc ag                                         32

<210> SEQ ID NO 2
<211> LENGTH: 30
<212> TYPE: DNA
<213> ORGANISM: human
<220> FEATURE:
<221> NAME/KEY: misc_feature
<223> OTHER INFORMATION: Reverse Primer pRK172/htau39

<400> SEQUENCE: 2
gatcggatcc gatatacata tggctgagcc                                            30

<210> SEQ ID NO 3
<211> LENGTH: 32
<212> TYPE: DNA
<213> ORGANISM: human
<220> FEATURE:
<221> NAME/KEY: misc_feature
<223> OTHER INFORMATION: Forward Primer pNG2 htau40

<400> SEQUENCE: 3
gatctctaga atcacaaacc ctgcttggcc ag                                         32

<210> SEQ ID NO 4
<211> LENGTH: 33
<212> TYPE: DNA
<213> ORGANISM: human
<220> FEATURE:
<221> NAME/KEY: misc_feature
<223> OTHER INFORMATION: Reverse Primer pNG2 htau40

<400> SEQUENCE: 4
gatcggatcc ggagatatac atatggctga gcc                                        33

<210> SEQ ID NO 5
<211> LENGTH: 34
<212> TYPE: DNA
<213> ORGANISM: mouse
<220> FEATURE:
<221> NAME/KEY: misc_feature
<223> OTHER INFORMATION: Forward Primer PERK.WT.9E10.p CDNA.amp

<400> SEQUENCE: 5
caggtcgact ctagaggcga tgtctgcaca aggc                                       34

<210> SEQ ID NO 6
<211> LENGTH: 35
<212> TYPE: DNA
<213> ORGANISM: mouse

```
<220> FEATURE:
<221> NAME/KEY: misc_feature
<223> OTHER INFORMATION: Reverse Primer PERK.WT.9E10.p CDNA.amp

<400> SEQUENCE: 6
cgataagctt gatatcggcc aggcagtggc gtgta                            35
```

PERK ACTIVATOR FOR THE TREATMENT OF NEURODEGENERATIVE DISEASES

This application is a national stage entry of International Application No. PCT/EP2015/068734, filed on Aug. 14, 2015, which claims priority from EP 14181071.3, filed on Aug. 14, 2014, the disclosures of which are incorporated herein by reference in their entirety to the full extent permitted by law.

The present invention relates to a novel method for the treatment and/or prophylaxis of neurodegenerative diseases and/or of neurodegenerative pathological conditions, especially of neurodegenerative diseases and/or of neurodegenerative pathological conditions which are a tauopathy and/or a disease and/or pathological condition associated with and/or accompanied by a tauopathy, preferably associated with and/or accompanied by tau aggregation, and in particular for the treatment and/or prophylaxis of a tauopathy. Compounds and/or agents and compositions for such treatment and/or prophylaxis, and the manufacture of the compounds and/or agents and compositions suitable for the said treatment and/or prophylaxis are also addressed. In this regard, the present invention relates especially to the use of compounds acting on PERK (protein kinase R-like endoplasmic reticulum kinase), a prodrug thereof, a derivative thereof and/or a pharmaceutically acceptable salt of any thereof, as a medicament.

BACKGROUND OF THE INVENTION

Worldwide, there are more than 35 million patients suffering from neurodegenerative diseases leading to dementia or movement disorders. Due to the increasing number of population with age above 65 there is a rising tendency (2050 above 50 million). Neurodegenerative diseases are usually caused by abnormal metabolization of proteins termed amyloidogenic in the central nervous system.

One prototypical representative of such disease-causing proteins is the microtubule-associated protein tau. Diseases associated with abnormal phosphorylation, pathological conformational change, aggregation (i.e. oligomerization, polymerization, and fibrillization) and accumulation in the somatodendritic compartment of the axonal microtubule-associated protein tau are called tauopathies.

Tauopathies are classified into primary and secondary tauopathies. Primary tauopathies include, but are not limited to, Progressive Supranuclear Palsy (PSP), Argyrophillic Grain Disease (AGD), Corticobasal Degeneration (CBD), Pick's Disease (PiD), and some other forms of frontotemporal lobar degenerations (FTLD).

The most frequent secondary tauopathy is Alzheimer's disease (AD). It is the most frequent neurodegenerative disease. It accounts for about 40% of the dementia cases, and about 60-80% of the tauopathies. The neuropathological hallmark of AD is the extracellular aggregation of the protein amyloid beta, which is generally believed to be the primary event leading to a secondary intracellular accumulation of the microtubule-associated protein tau in the central nervous system.

All of these disorders are progressive in nature and lead to severe functional impairments, major individual and social burden, and ultimately death of the affected patient.

For all these diseases, currently available therapeutic options are essentially limited to transient and incomplete symptomatic improvements. There is no approved disease-modifying, neuroprotective medical intervention available, which would allow retarding or ideally stopping the progression of the disorder, based on an intervention at the level of essential disease mechanisms, but there exists a huge clinical demand.

On the other hand, for treating patients with neurodegenerative diseases, different compounds for diverse targets are currently in various phases of clinical development, including clinical testing of tau-based therapeutic strategies in manifold approaches. Previously described approaches aiming at the development of neuroprotective treatment of tauopathies include diverse strategies, such as mitochondrial enhancers (e.g. coenzyme Q10), inhibitors of tau kinases (e.g. tideglusib), inhibitors of O-GlcNAcase, stabilizators of microtubules (e.g. davunetide, epothilone D), antiaggregational compounds (e.g. anle 138b), tau-antibodies. None of those approaches, which made their way into a clinical trial, has shown efficacy in patients so far (Poewe et al. 2015).

A number of companies, amongst them larger ones (like AbbVie, BMS, UCB, Roche), but also smaller biotech companies like Asceneuron (OGA inhibition), TauRx (methylene blue), Déclion Pharmaceuticals (PSP; detoxification), Chronos Therapeutics (AD, PSP), Treventis Corp. (AD, PSP; anti-aggregants), Summit Therapeutics Plc. (OGA inhibition), Proteo Tech (PSP), Selvita (AD, tauopathies; DYRKIA kinase inhibitor) and Sellas Biopharmaceuticals (PSP; GABA-A-BZ1 receptor agonist), but also universities (PSP, CBD, 4R-tauopathies; stabilization of microtubules) have (pre-) clinical programs against tauopathies in the development.

The international patent publication WO 2013/192165 proposed to treat neurodegenerative diseases with compounds selectively activating the apoptotic but not the adaptive arm of the unfolded protein response. Reference is made to Chung et al. 2013 (WO2013/192165). Thus, the method aims to selectively activate the apoptotic arm of the unfolded protein response and subsequent apoptotic cell death, whereas, as shown in the detailed description the method of the present invention inversely is demonstrated to prevent rather than to induce cell death through the activation of PERK. The WO 2013/192165 also mentions PERK to be implicated in the unfolded protein response pathway; however, it does not provide any evidence at all that the referenced compounds are indeed PERK activators, which in contrast is the mode of action focused in the present patent application.

Furthermore, concerning PERK, in the prior art the dominant opinion prevails in that neurodegenerative diseases, if anything, should be treated by inhibition of PERK. Reference is made, for example, to the scientific articles: Axten et al. 2012; Ma et al. 2013; Moreno et al. 2013; Pytel et al. 2014; Scheper et al. 2015.

In the prior art, some authors have proposed to stimulate PERK or to activate signaling cascades downstream of PERK to treat neurodegenerative diseases caused by abnormal metabolization of the protein amyloid-beta or the prion protein. Reference is made, for example, to the scientific articles: Lee do et al. 2010; Stockwell et al. 2012.

One prior work suggested that inhibition of PERK would reduce tauopathy. Reference is made to: van der Harg et al. 2014.

However, no prior work has proposed to activate PERK to treat tauopathies, i.e. neurodegenerative diseases induced by abnormal metabolization of the tau protein.

In summary, today there is no approved medical treatment for neurodegenerative tauopathies based on an intervention at the level of essential disease mechanisms, which would allow retarding or ideally stopping the progression of the disorder. There were only few past attempts to address these limitations. None of these interventions fulfilled the criteria of a disease-modifying, neuroprotective intervention in a clinical trial so far.

The object underlying this intervention is the development of a new rational method to ameliorate symptoms and retard disease progression in tauopathies. Another object of the invention is the development of a new rational method to ameliorate symptoms and retard disease progression in tauopathies for treating and/or preventing tauopathies, i.e. primary and/or secondary tauopathies, especially in a patient population suffering from neurodegenerative diseases and/or neurodegenerative conditions, which are at least partially, preferably predominantly, associated with abnormal phosphorylation, pathological conformational change, aggregation (i.e. oligomerization, polymerization, and fibrillization) and accumulation in the somatodendritic compartment of the axonal microtubule-associated protein tau.

Particularly, the object of the present invention is to overcome the reluctance and prejudice in the prior art and to provide new and efficient therapies for the treatment and/or prophylaxis of neurodegenerative diseases and/or of neurodegenerative pathological conditions in higher mammals, particularly in humans, especially of neurodegenerative diseases and/or of neurodegenerative pathological conditions associated with and/or accompanied by tau aggregation. A particular object of the present invention is to provide new and efficient therapies for the treatment and/or prophylaxis of a tauopathy. A further object of the present invention is to provide compounds and/or agents and compositions for such treatment and/or prophylaxis, and the manufacture of the compounds and/or agents and compositions suitable for the said treatment and/or prophylaxis. In this regard, the object of the present invention relates especially to the use of compounds acting as PERK activator, a prodrug thereof, a derivative thereof and/or a pharmaceutically acceptable salt of any thereof, as a medicament in higher mammals, particularly in humans.

SUMMARY OF THE INVENTION

The present invention is defined in any one of the claims, and it is based on the new findings and profound data as produced by the inventors for the first time and shown herein after. Compared to the described prior art, the invention relates to compounds distinctly acting on a kinase called PERK (protein kinase R-like endoplasmic reticulum kinase) as a new therapeutic approach to treat tauopathies.

Particularly, the solution provided by the invention relates to the direct and/or indirect stimulation and/or activation, preferably to the direct stimulation and/or activation, of PERK as a new therapeutic approach in the treatment and/or prophylaxis of tau-mediated neurodegenerative diseases and/or of tau-mediated neurodegenerative pathological conditions, and in particular in the treatment and/or prophylaxis of tauopathies. This direct and/or indirect stimulation and/or activation of PERK in the present invention, which aims at protecting neuronal cells from damage and death, is in contrast to the prior art on PERK which describes the inhibition rather than activation of PERK, or which describes PERK in a context to induce rather than to inhibit apoptosis, or activation of signaling cascades downstream of PERK rather than acting on PERK itself, or which describes PERK activation for the treatment of conditions other than tau-mediated diseases, i.e. tauopathies.

The invention provides a surprisingly novel therapeutic approach for the treatment and/or prophylaxis of a tau-mediated neurodegenerative disease and/or of a tau-mediated neurodegenerative pathological condition, e.g. in higher mammals, particularly in humans. Especially, the invention provides a new rational method to ameliorate symptoms and retard disease progression in tauopathies for treating and/or preventing tauopathies, i.e. primary and/or secondary tauopathies, especially in a patient population suffering from a neurodegenerative disease and/or condition, which is at least partially, preferably predominantly, associated with abnormal phosphorylation, pathological conformational change, aggregation (i.e. oligomerization, polymerization, and fibrillization) and accumulation in the somatodendritic compartment of the axonal microtubule-associated protein tau.

Preferably the invention provides a new rational method to ameliorate symptoms and retard disease progression in tauopathies, and for treating and/or preventing tauopathies, and/or for the treatment and/or prophylaxis of a neurodegenerative disease and/or of a neurodegenerative pathological condition associated with and/or accompanied by tau aggregation, e.g. in higher mammals, particularly in humans. In the context of the invention, in particular tauopathies are classified into primary and secondary tauopathies. Primary tauopathies include, but are not limited to, Progressive Supranuclear Palsy (PSP), Argyrophillic Grain Disease (AGD), Corticobasal Degeneration (CBD), Pick's Disease (PiD), and some other forms of frontotemporal lobar degenerations (FTLD).

Accordingly, the invention relates in one aspect to a compound or compound classes which are functionally defined as a direct and/or indirect, more preferably as a direct, PERK activator, a prodrug thereof, a derivative thereof and/or a pharmaceutically acceptable salt of any thereof, wherein the compound is for use in the treatment and/or prophylaxis of a tau-mediated neurodegenerative disease and/or of a tau-mediated neurodegenerative pathological condition. Preferably, the invention relates to a compound or compound classes which are functionally defined as a direct and/or indirect, more preferably as a direct, PERK activator, wherein the compound is for use in the treatment and/or prophylaxis of a neurodegenerative disease and/or of a neurodegenerative pathological condition associated with abnormal phosphorylation, pathological conformational change, aggregation (i.e. oligomerization, polymerization, and fibrillization) and accumulation in the somatodendritic compartment of the axonal microtubule-associated protein tau, preferably for use in the treatment and/or prophylaxis of a tauopathy; and/or wherein the compound is for use in the treatment and/or prophylaxis of a neurodegenerative disease and/or of a neurodegenerative pathological condition associated with and/or accompanied by tau aggregation, e.g. in higher mammals, particularly in humans.

The surprising finding of the present invention, as shown and supported by the experimental data and evidence provided by the inventors herein for the first time, was obtained by investigating the PERK activating compound CCT020312, which is the first supposedly selective PERK activating compound that became known in the public, functionally and structurally, and thus served the inventors as a general representative for compound classes characterized functionally as PERK activators. Thus, the concept of PERK activation according to the present invention is broadly applicable to each and any PERK activating compound class. Reference is made to FIG. 1, which is contrasting the classical canonical pathway (A) vs. the unique finding of the present invention pertaining to PERK activating compounds, i.e. the PERK pathway in the prototypical tauopathy PSP (B) and the changes induced by the PERK activator in cell models of tauopathies (C). After the invention was made, some further PERK activating compounds were disclosed in the scientific literature, but without any reference to tauopathy; see Xie et al. 2015. The authors of this article mention as targeted diseases cancer, diabetes, (likely beta-amyloid-pathology in) Alzheimer's disease, and in particular COPD (chronic obstructive pulmonary disease), whereas they do neither address nor realize any tau-mediated neurodegenerative disease and/or neurodegenerative condition, which in contrast are at the heart of the present invention.

Accordingly, based on the broad and unique mechanistic finding on the present invention, the term "PERK activator" or "PERK activating compound" according to the present invention, independently from any structural feature, i.e. from any compound formula, is functionally defined as a compound that stimulates the kinase activity of PERK protein and/or as a compound for use in method to stimulate the kinase activity of PERK protein; and preferably as a compound that stimulates the kinase activity of PERK protein and/or as a compound for use in method to stimulate the kinase activity of PERK protein; as determined by increased phosphorylation of its target proteins eukaryotic translation initiation factor 2-alpha (EIF2A) and/or nuclear factor erythroid 2-related factor 2 (NRF2).

A suitable identification and characterization of "PERK activator" or "PERK activating compound" is, for example, possible by phenotypic screening as described by Xie et al. 2015. This assay measures phosphorylation of GFP-tagged EIF2A upon PERK activation via a cell-based LanthaScreen technology. It is a robust assay with sufficient signal to background and low variation, wherein multiple parameters are optimized including GFP-tagged EIF2A BacMam concentration, cell density and serum concentration. The assay is validated by a tool compound, thapsigargin, which induces phosphorylation of EIF2A by induction of endoplasmic reticulum stress, thereby indirectly activating PERK. It is possible to identify PERK activators through phosphorylation of EIF2A or NRF2, i.e. by performing focused compound screenings in this assay at e.g. 10 µM, and thereby compound hits, i.e. PERK activators, are easily identified and validated.

In a further aspect, the invention also relates to a pharmaceutical composition comprising said compound as a direct and/or indirect, more preferably as a direct, PERK activator, a prodrug thereof, a derivative thereof and/or a pharmaceutically acceptable salt of any thereof, for the said treatment and/or prophylaxis, e.g. in higher mammals, particularly in humans.

In another aspect, the invention also relates to a method of treatment and/or prophylaxis, wherein the said compound acting as a PERK activator and/or a pharmaceutical composition comprising said compound as a direct and/or indirect, more preferably as a direct, PERK activator, a prodrug thereof, a derivative thereof and/or a pharmaceutically acceptable salt of any thereof, for the said treatment and/or prophylaxis, e.g. in higher mammals, particularly in humans.

The invention is based on the novel and surprising finding by the inventors that the activation of PERK enables novel therapies for the treatment and/or prophylaxis of tauopathies. According to the invention a novel mechanism is described for reducing tauopathy-induced tau-aggregation after tau-phosphorylation and subsequent change of confirmation. A new treatment and/or prophylaxis is proposed based on this disease related tau protein accumulation. In the context of this invention the disease PSP is investigated as a prototypical model of tauopathy, which is characterized by aggregation of hyperphosphorylated tau protein with predominance of isoforms with 4 microtubule-binding repeats (4R-tau). Depending on the isoform various different tau-deposition products exist.

The disease categorization referring to tau isoforms is made according to the number of certain repetitions at the microtubule binding site. According to the number of microtubule-binding repeats (3R vs. 4R), tauopathies are classified in 3R- or 4R-tauopathies. PSP is a rare disease (6/100000 persons), but due to similar symptoms it is related in its characteristics to Parkinson's disease. The cause of PSP is assumed to be a genetic predisposition, a finding revealed by the inventors of the present invention a few years ago. Further examples of tauopathies, as defined herein, are described in the present invention, are commonly characterized by aggregation of hyperphosphorylated 3R, 4R as well as mixed forms of tau proteins.

The inventors have established data based on which they concluded on a modified pathway as integral part of the stress-related "unfolded protein response" (UPR) for PSP, as compared to the canonic PERK pathway. Regarding the modified pathway it is supposed that EIF2A in PSP is inhibited, and thereby the therapeutic PERK activation may be beneficial as a compensatory intervention. In PSP-affected brains, it was possible to show that along with an upregulation of phosphorylated (activated) PERK the additional factor NRF2 is phosphorylated (activated), which alternatively effects the protection against a stress response by an amelioration of cell survival. The inventors were able to impressively show in cell culture that administering a PERK activator (CCT020312) to cells overexpressing 4R-tau in contrast to a PERK inhibitor substantially increased the activation of NRF2 and as a consequence of this significantly declines the 4R-tau-mediated toxicity. Furthermore, it was shown in vitro, that phosphorylation of 4R-tau, the basis of the disease causing tau aggregates, can be significantly diminished by the PERK activator.

The in vitro findings of the present invention were also confirmed by in vivo data showing that PERK activation mitigates tau pathology in P301S MAPT transgenic mice, and by histological demonstration of tau-pathology in a brain autopsy of a human without PERK function, showing the effects of PERK dysfunction in WRS (Wolcott-Rallison Syndrome; see Bruch et al. 2015: Early Neurodegeneration in the Brain of a Child Without Functional PKR-like Endoplasmic Reticulum Kinase.), thus complementing the findings in the animal models and short-term cell culture models.

In the following the invention shall be described in more detail.

b) Hypothetical PERK pathway in PSP. In PSP brains and in human neurons overexpressing 4R-tau or treated with annonacin, we found a decrease in total and phosphorylated (i.e. activated) EIF2A protein levels. We also found an up-regulation of total PERK and phosphorylated (activated) PERK (pPERK), and NRF2, which might be an attempt of secondary compensation for reduced EIF2A.

c) Changes induced by the PERK activator in cell models of PSP. In the tauopathy cell models used, the PERK activator CCT020312 (Pa) induced phosphorylation of NRF2. This in turn leads to increased cell health and promoted cell survival.

Figure 2:
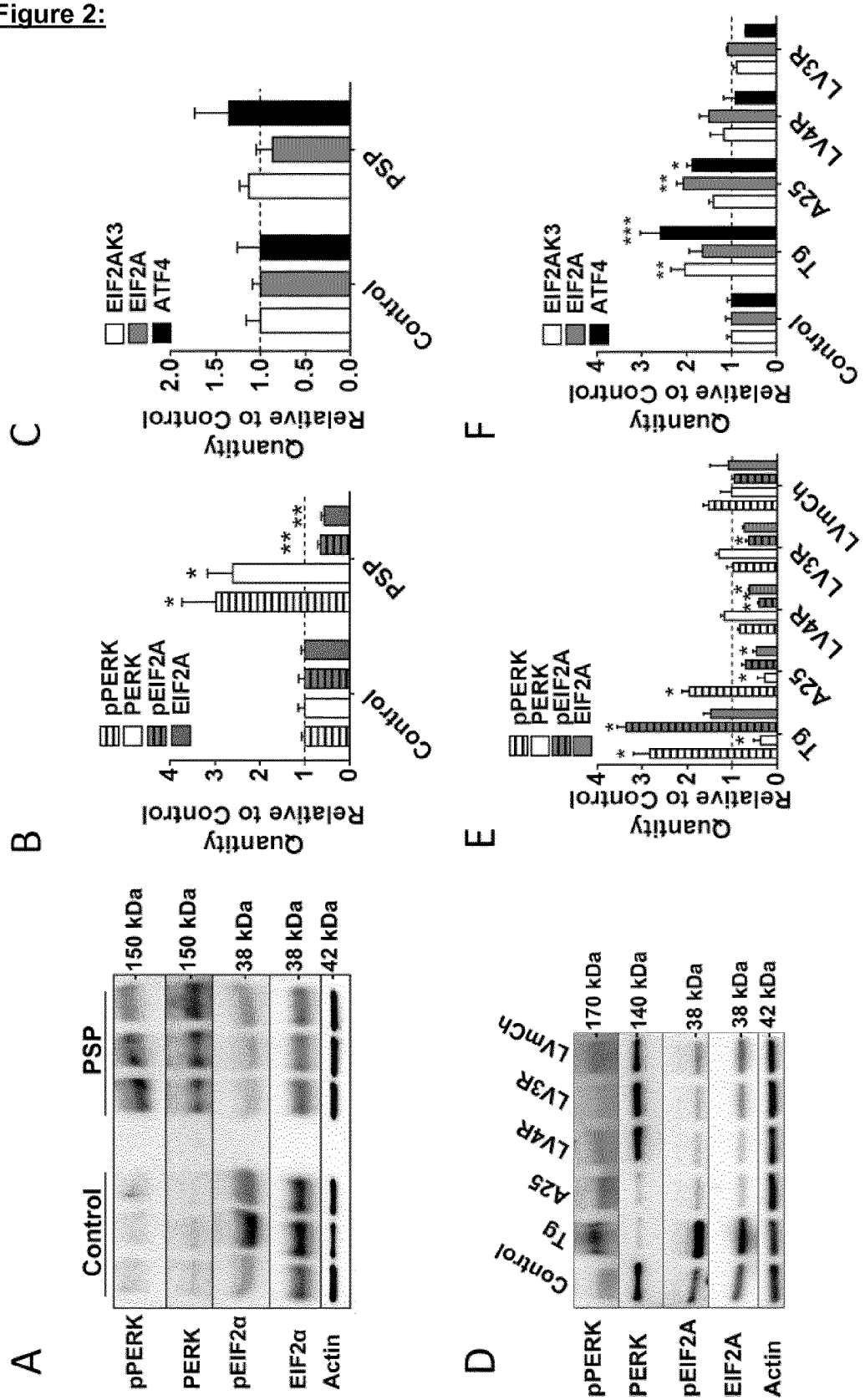

FIG. 2: The State of the Unfolded Protein Response in PSP and in Two Models of Tauopathy a) Representative Western blots of *gyrus frontalis* superior tissue of three PSP patients and three controls without neurodegenerative disorder. 200 μg protein was loaded for pPERK, 20 μg protein for the other antibody incubations.

b) Quantification of Western blot results as shown in FIG. 2A (PSP: n=7; controls: n=3; details in Table 4). t-Tests with Sidak-Bonferroni correction; * $p<0.05$,  $p<0.01$, * $p<0.001$, PSP vs. control.

c) Results from quantitative PCR performed on mRNA obtained from the same tissues (PSP: n=7; control: n=3). t-Tests with Sidak-Bonferroni correction showed no significant differences.

d) Representative Western blots of differentiated LUHMES neurons after 48 h treatment with 30 nM thapsigargin (Tg, positive control) or 25 nM annonacin (A25), or after 8 days lentiviral overexpression of 4R-tau (LV4R), 3R-tau (LV3R) or mCherry (LVmCh).

e) Quantification of Western blot results as shown in FIG. 2D relative to untreated control cells (n=3 per group). 2-way ANOVA with Dunnett's post-hoc test: * $p<0.05$, ** $p<0.01$, vs. control (untreated cells).

f) Results from quantitative PCR performed on mRNA obtained from the same cell extracts as the blots in 2E (n=3 per group). 2-way ANOVA with Dunnett's post-hoc test vs. control (untreated cells). * $p<0.05$,  $p<0.01$, * $p<0.001$, vs. control (untreated cells).

Figure 3:
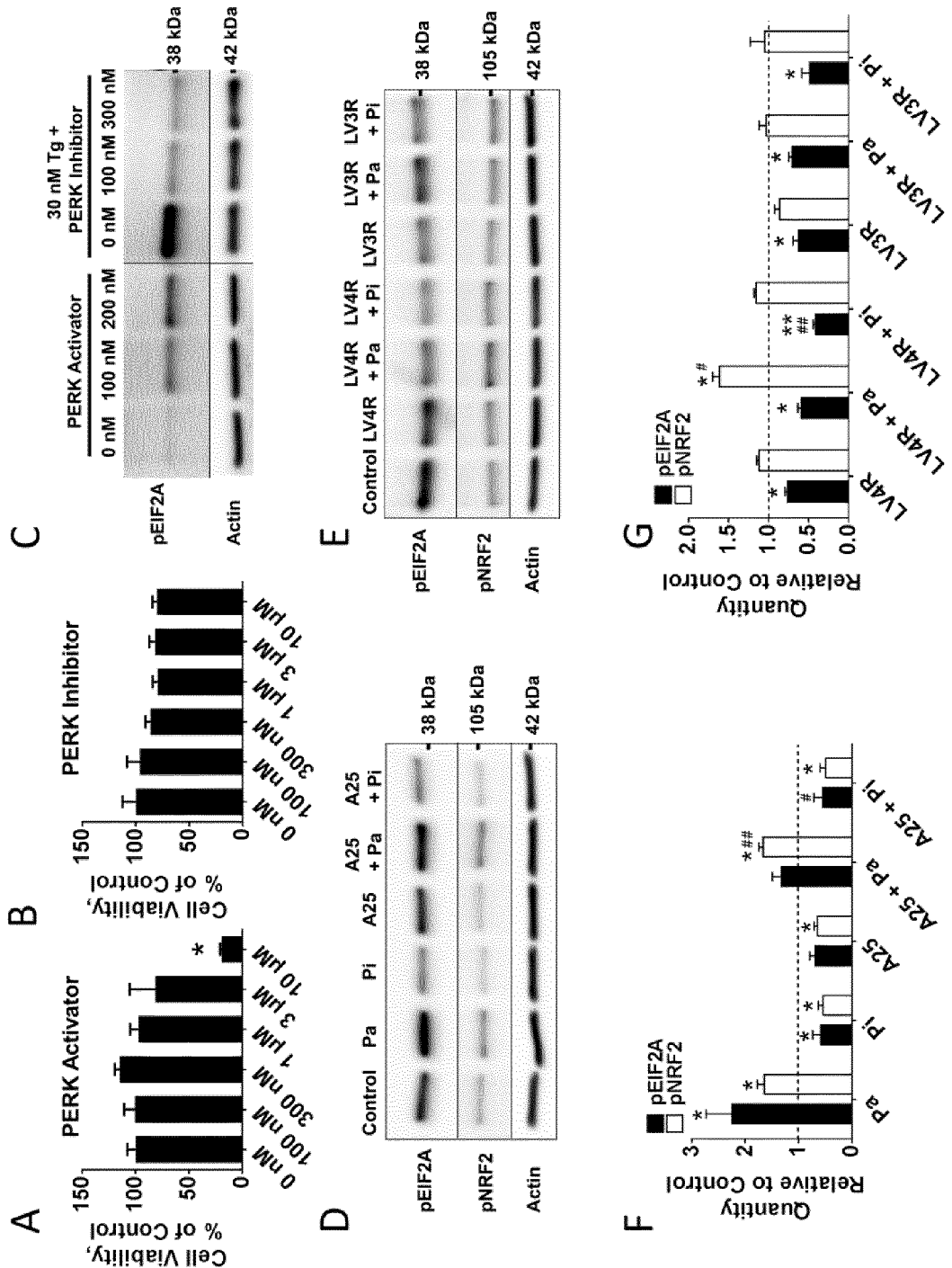

FIG. 3: PERK Activator and PERK Inhibitor Modulate EIF2A and NRF2 Phosphorylation.

a) MTT cell viability assay of LUHMES cells treated for 48 h with different concentrations of PERK activator CCT020312.

b) MTT cell viability assay of LUHMES cells treated for 48 h with different concentrations of PERK inhibitor GSK2606414.

c) Western blots for phosphorylated EIF2A (pEIF2A) and actin of LUHMES cells treated for 48 h with two different concentrations of PERK activator (left half) or 30 nM thapsigargin (Tg) to phosphorylate EIF2A and two different concentrations of PERK inhibitor (right half).

d) Western blots for pEIF2A, phosphorylated NRF2 (pNRF2) and actin of LUHMES cells left untreated (control) or treated for 48 h with 200 nM PERK activator (Pa), 300 nM PERK inhibitor (Pi) or 25 nM annonacin (A25) or a combination. Please note that all bands for one antibody are from the same blot, but that their order was changed without further modifications, to achieve a consistent presentation.

e) Western blots for pEIF2A, pNRF2 and actin of LUHMES cells left untreated (control) or treated with lentivirus, as indicated for 8 days, and 200 nM PERK activator (Pa) or 300 nM PERK inhibitor (Pi).

f) Quantification of Western blots as in FIG. 3D with three different biological repeats. 2-way ANOVA with Dunnett's post-hoc test: * $p<0.05$, # $p<0.05$, ## $p<0.01$ vs. A25 without PERK modulator.

g) Quantification of Western blots as in FIG. 3E with three different biological repeats. 2-way ANOVA with Dunnett's post-hoc test: * $p<0.05$, ** $p<0.01$ vs. control; # $p<0.05$, ## $p<0.01$ vs. LV4R or LV3R, resp., without PERK modulator.

Figure 4:
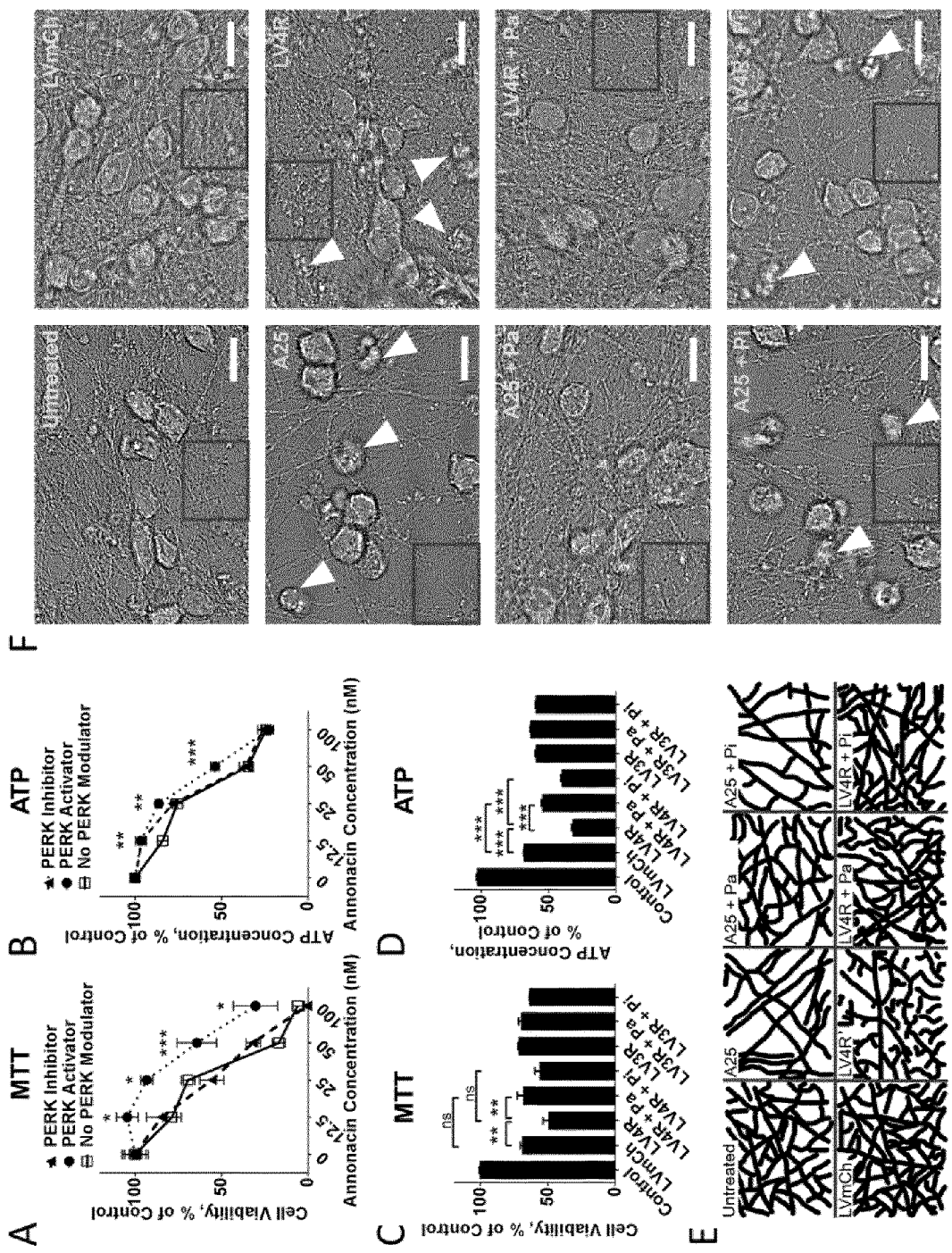

FIG. 4: Different Indicators of Toxicity in 4R-Tau- and Annonacin-Treated LUHMES Cells.

a) MTT assay on LUHMES neurons treated for 48 h with different concentrations of annonacin and either PERK inhibitor, PERK activator or no PERK modulator. 2-way ANOVA with Dunnett's post-hoc test: * $p<0.05$,  $p<0.01$, * $p<0.001$ PERK activator vs. no PERK modulator. PERK inhibitor vs. no PERK modulator was never significant.

b) ATP concentration in LUHMES neurons treated for 48 h with different concentrations of annonacin and either PERK inhibitor, PERK activator or no PERK modulator. 2-way ANOVA with Dunnett's post-hoc test: * $p<0.05$,  $p<0.01$, * $p<0.001$ PERK activator vs. no PERK modulator. PERK inhibitor vs. no PERK modulator was significant only at an annonacin concentration of 12.5 nM ($p<0.01$).

c) MTT assay on LUHMES neurons treated for 10 days with different lentiviruses (LVmCh=mCherry, LV4R=4R-tau, LV3R=3R-tau) and either PERK inhibitor (Pi), PERK activator (Pa) or no PERK modulator. Control=untreated cells of same age. 1-way ANOVA with Tukey's post-hoc test: ** $p<0.01$, ns=not significant.

d) ATP concentration of LUHMES neurons treated for 10 days with the lentivirus shown and either Pi, Pa or no PERK modulator. 1-way ANOVA with Tukey's post-hoc test: *** $p<0.001$.

e) Neuritic network of 10 day old LUHMES neurons that were either treated with 25 nM annonacin (A25) and Pa or Pi for 48 h or with LV4R and Pa or Pi for 10 days. Untreated cells and cells treated with LVmCH were used as controls.

f) Microscopic bright-field (grey) and overlaid DAPI images of 10 day old LUHMES neurons that were either treated with 25 nM annonacin and Pa or Pi for 48 h or with LV4R and Pa or Pi for 10 days. Scale bar=100 μm. The areas marked with red boxes indicate the location of the neuritic network shown in FIG. 4E. White arrows point towards apoptotic cells with condensation of DNA to chromatin clumps.

Figure 5:
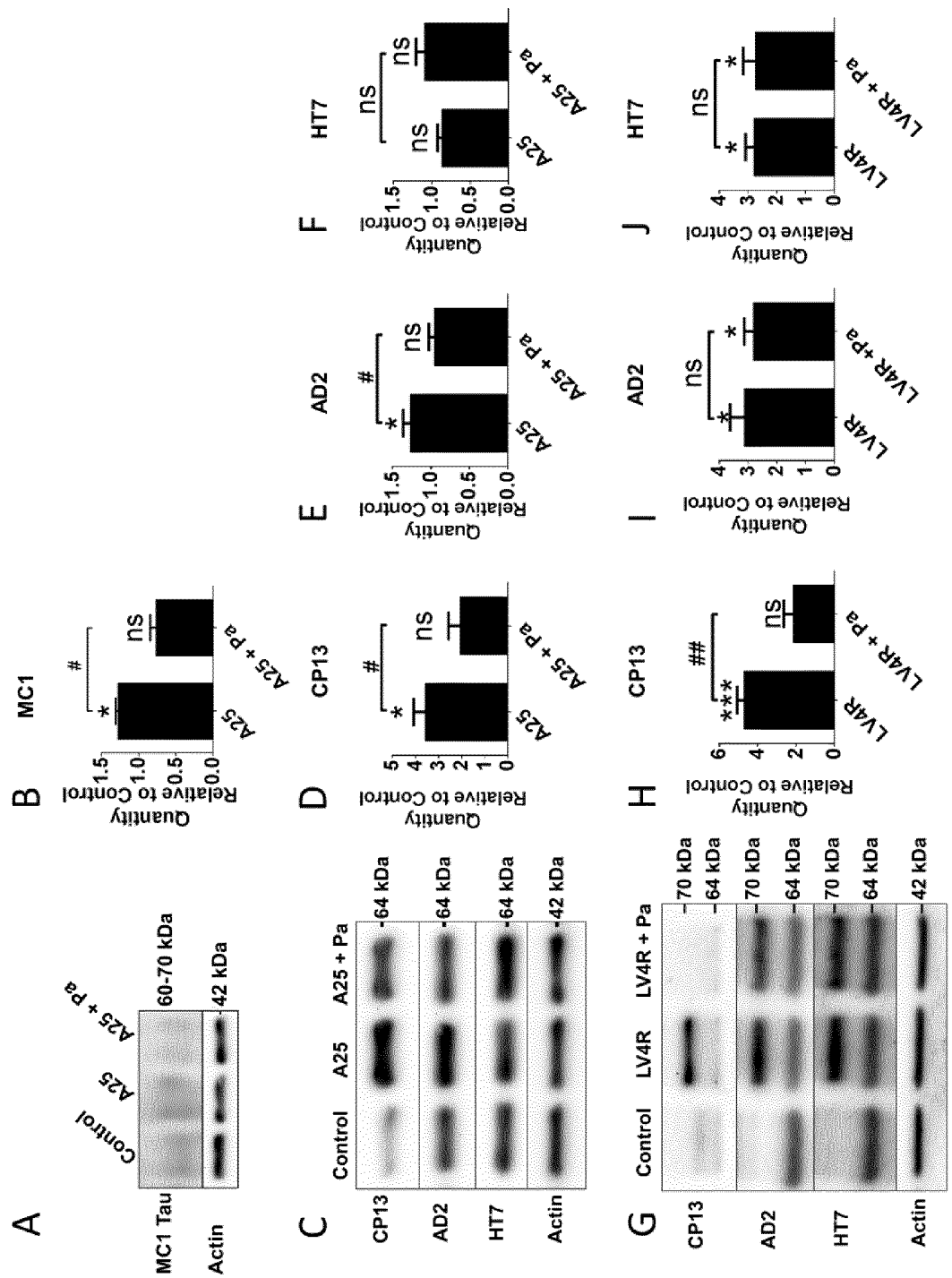

FIG. 5: The Effect of PERK Activator on Pathological Tau Conformation and Phosphorylation a) Representative Western blots of LUHMES neurons treated with 25 nM annonacin (A25) for 48 h in absence or presence of the PERK activator (Pa), using the MC1 antibody, recognizing tau with pathological conformation. Actin is shown as loading control. A25 increased the MC1 signal, and Pa averted it.

b) Quantification of three biological replicates of Western blots, as shown in FIG. 5A.

c) Representative Western blots of LUHMES neurons treated with A25 for 48 h in absence or presence of the Pa, using antibodies recognizing tau phosphorylated at different epitopes (CP13: Serine 202; AD2: Serine 396), total tau (HT7) and actin (loading control).

d-f) Quantification of three biological replicates of Western blots, as shown in FIG. 5C. ANOVA with Dunnett's post-hoc test; * $p<0.05$,  $p<0.01$, * $p<0.001$ vs. control; # $p<0.05$ A25 vs. A25+Pa, ns: not significant.

g) Representative Western blots of LUHMES neurons after overexpression of 4R-tau for 8 days in absence or presence of the Pa, using the antibodies CP13, AD2, HT7 and actin. Note that the transgenic 4R2N-tau runs at 70 kDa and the endogenous tau around 64 kDa.

h-j) Quantification of three biological replicates of Western blots, as shown in FIG. 5G. ANOVA with Dunnett's post-hoc test; * $p<0.05$,  $p<0.01$, * $p<0.001$ vs. control; ##: $p<0.01$ LV4R vs. LV4R+Pa, ns: not significant.

Figure 6:
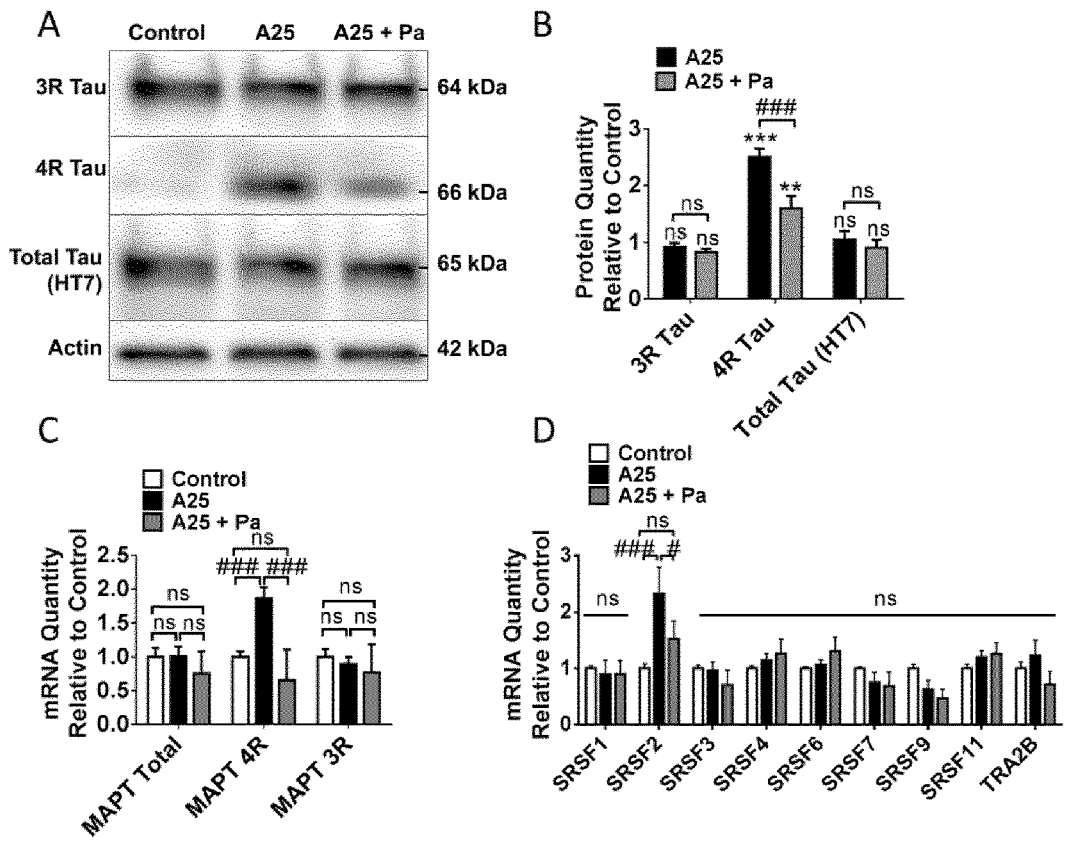

FIG. 6: PERK Activator Reduces 4R-Tau Expression by Reducing SRSF2 Expression a) Representative Western blot of LUHMES neurons treated for 48 h with 25 nM annonacin (A25) in presence or absence of the PERK activator (Pa) using antibodies recognizing 3R-tau isoforms, 4R-tau isoforms, total tau (HT7) or actin (loading control).

b) Quantification of three biological replicates of Western blots, as shown in FIG. 6A. ANOVA with Dunnett's post-hoc test: * $p<0.05$,  $p<0.01$, * $p<0.001$ vs. control; ### $p<0.001$ A25 vs. A25+Pa, ns: not significant.

c) Quantitative PCR results for 3R MAPT, 4R MAPT and total MAPT mRNA in differentiated LUHMES neurons treated as indicated for 48 h. Control cells were left untreated. 2-way ANOVA with Dunnett's post-hoc test: ### $p<0.001$; ns: not significant.

d) Quantitative PCR results for mRNA of splicing factors implicated in MAPT exon 10 alternative splicing (i.e. the shift between 3R and 4R-tau isoforms) in LUHMES neurons treated as indicated. 2-way ANOVA with Dunnett's post-hoc test: # $p<0.05$, ### $p<0.001$; ns: not significant.

Figure 7:
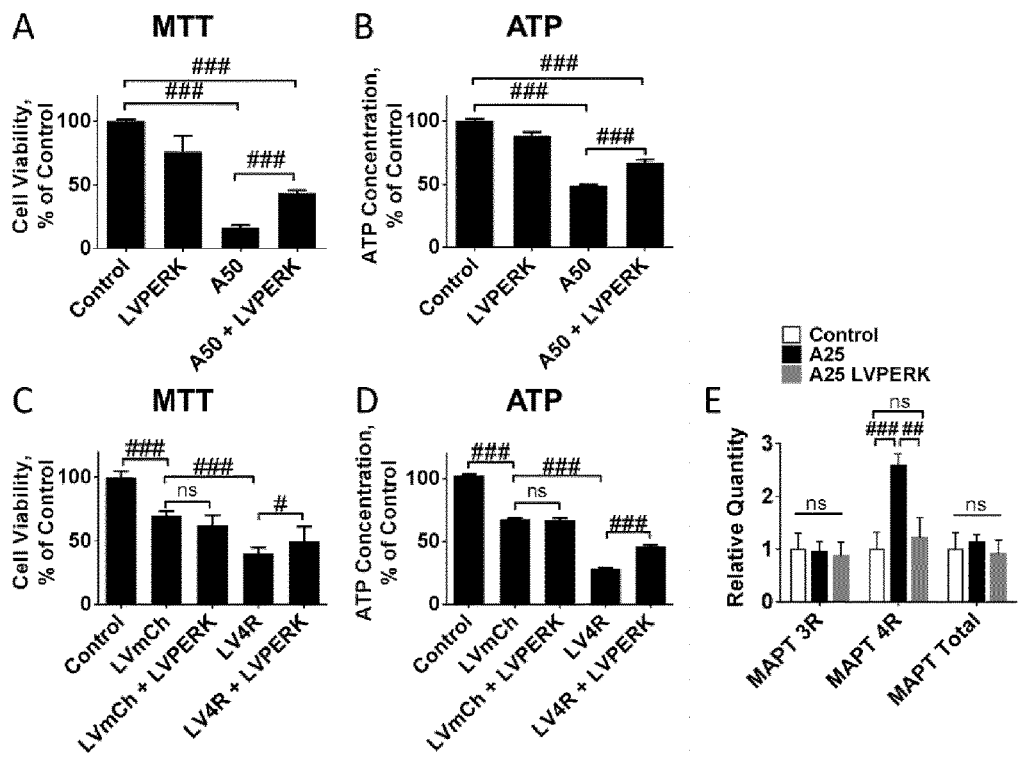

FIG. 7: The Effects of the PERK Activator can be Reproduced by Lentiviral Overexpression of PERK.

a, b) MTT and ATP assay of LUHMES neurons treated as indicated (A50=50 nM annonacin, Pa=PERK activator, LVPERK=lentivirus overexpressing wild type PERK). Annonacin treatment was for 48 h from 8 days post differentiation. LVPERK treatment was from 6 h after initiation of differentiation. 2-way ANOVA with Tukey's post-hoc test. ### $p<0.001$, ns: not significant.

c, d) MTT and ATP assay results of LUHMES neurons treated as indicated (LV4R=lentivirus overexpressing 4R-tau). Lentiviral treatment was from 6 h after initiation of differentiation. 2-way ANOVA with Tukey's post-hoc test. # $p<0.05$, ### $p<0.001$, ns: not significant.

e) Quantitative PCR results of 10 days differentiated LUHMES neurons for 3R, 4R and total MAPT mRNA. Annonacin treatment was for 48 h from day 8. LVwt-PERK treatment was 6 h after initiation of differentiation. Control cells were left untreated. 2-way ANOVA with Tukey's post-hoc test. ## $p<0.01$, ### $p<0.001$, ns: not significant.

Figure 8:
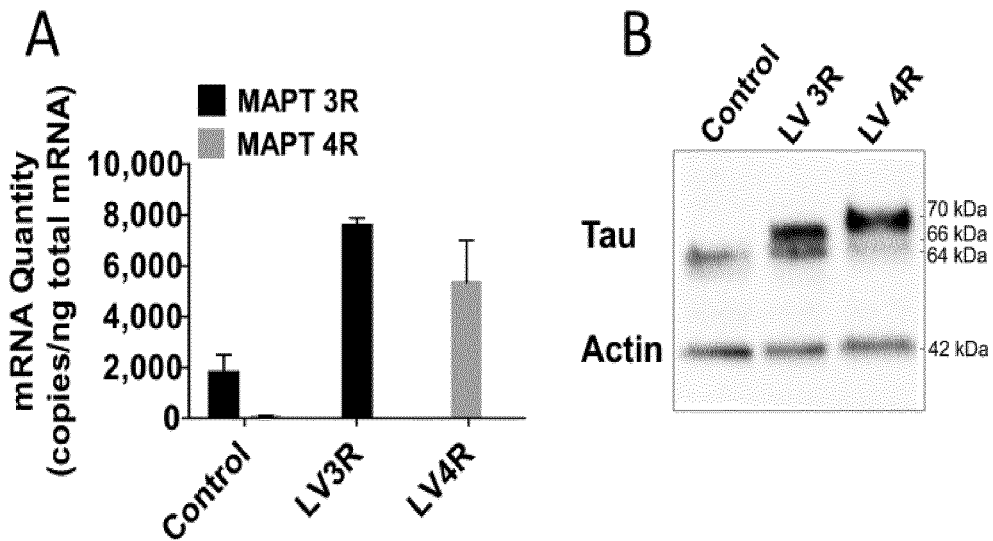

FIG. 8: Wild Type Tau Overexpression Model a) Absolute quantification by qPCR of the amount of 3R and 4R spliced MAPT mRNA existent in 8 days old LUHMES neurons either left untreated (control) or treated with lentivirus overexpressing 3R-tau (LV3R) or 4R-tau (LV4R).

b) Western blot for total tau (HT7 antibody) and beta-actin showing the overexpression of different isoforms of tau when LUHMES cells are incubated for 8 days with lentiviruses to overexpress either 3R (LV3R) or 4R (LV4R) tau. The most strongly expressed isoform in LUHMES cells at this stage of differentiation is the 3R isoform running at 64 kDa. The 3R2N isoform overexpressed by LV3R runs at 66 kDa, whilst the 4R2N isoform overexpressed by LV4R runs at 70 kDa.

Figure 9:
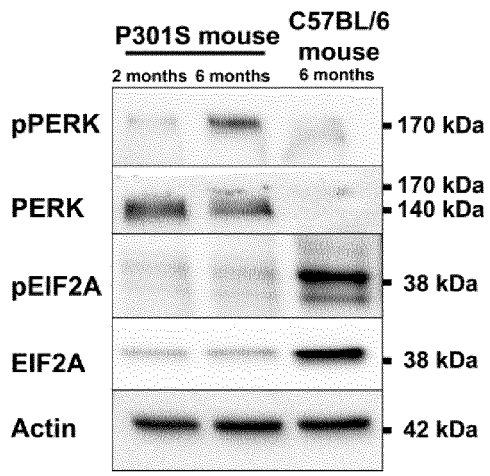

FIG. 9: Changes in pPERK, PERK, pEIF2A and EIF2A in P301S Tau Transgenic Mice.

Western Blot of whole brain extract of a 2 and 6 month old P301S mouse and a 6 month old C57BL/6 control mouse. 200 μg of protein was loaded for the pPERK blot, 20 μg of protein for all other blots.

Figure 10A:
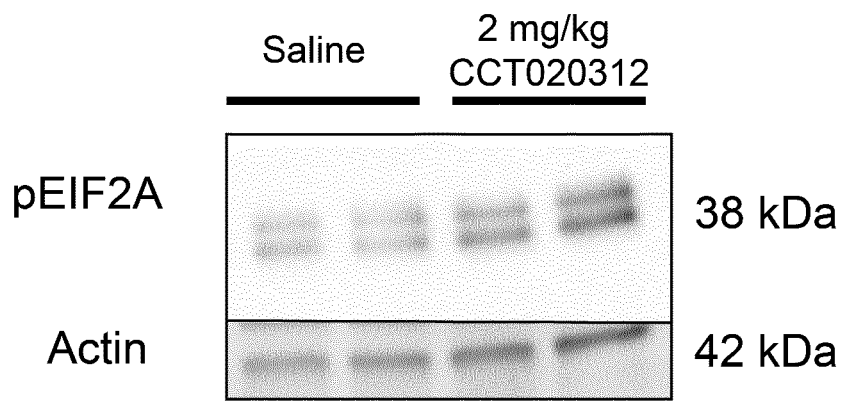

FIG. 10A: Systemic Administration of CCT020312 Increases EIF2A Phosphorylation in Mouse Brain Tissue In vivo, Suggesting Blood Brain Barrier Penetration and Target Engagement.

Wild type mice were injected intraperitoneally once daily for three consecutive days with 2 mg/kg body weight of the PERK activator CCT020312. Western blots of whole brain homogenates were done for phosphorylated EIF2A (pEIF2A). EIF2A is a substrate to the kinase activity of PERK. Actin was used as loading control. Note that the drug lead to a marked increase in pEIF2A compared to saline treatment.

FIG. 10B: Systemic Short-term Administration of CCT020312 Increases Phosphorylated PERK in Wild-type Mouse Brains in Dose-dependent Manner, Suggesting Brain Penetration and Target Engagement.

Wild type mice at 15 weeks of age (n=3 per group) were injected intraperitoneally once daily for three consecutive days with the PERK activator (PA) CCT020312 in doses of 1, 2, or 5 mg/kg. Western blots of whole brain homogenates (left panel) were done with antibodies raised against phosphorylated PERK (pPERK), PERK, phosphorylated NRF2 (pPERK), or NRF2. GAPDH was used as loading control. Quantification of the blots and normalization to GAPDH demonstrated that drug treatment significantly increased pPERK compared to saline treatment. One way ANOVA followed by post hoc LSD test, * $P<0.05$, ** $P<0.01$.

FIG. 10C: Systemic Long-term Administration of CCT020312 Increases Phosphorylated PERK in Wild-type Mouse Brains.

Wild type mice were injected intraperitoneally once daily for 6 weeks starting at 9 weeks of age with PERK activator (PA) CCT020312 (2 mg/kg) or saline (SA) (n=3 per group). Western blots of whole brain homogenates (left panel) were done for pPERK, PERK, pNRF2, NRF2. GAPDH was used as loading control. Quantification of the blots (right panel) and normalization to GAPDH demonstrated that drug treatment significantly increased pPERK and pNRF2 compared to SA treatment, while no significant upregulation was observed for total PERK and total NRF2. t-Test, * $P<0.05$.

Figure 11A:
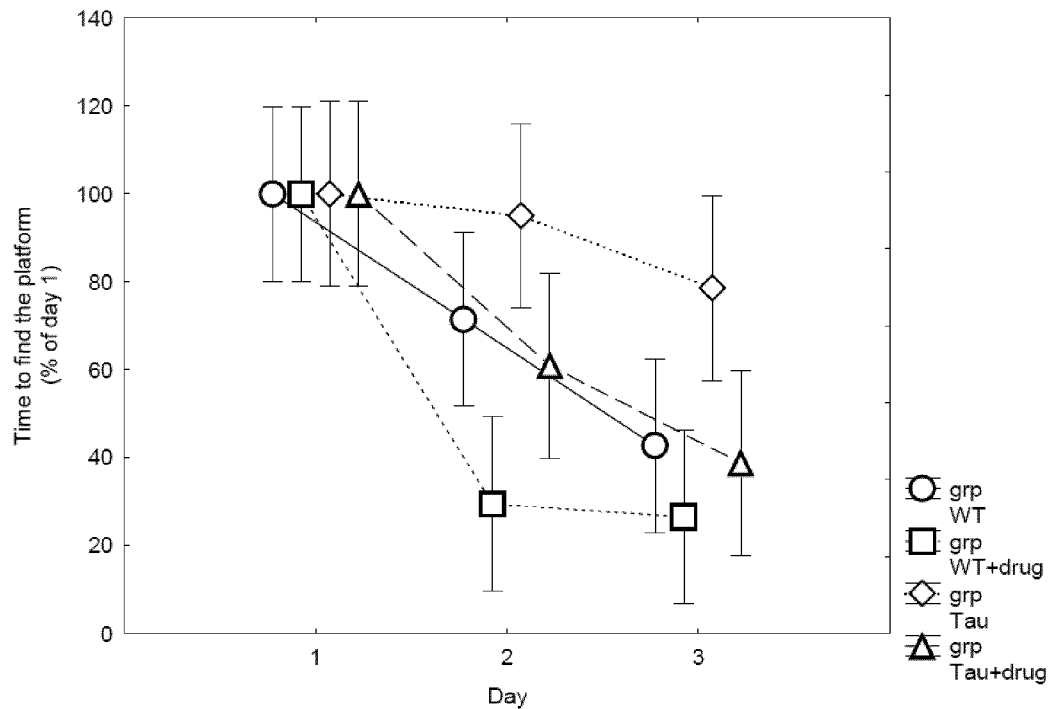

FIG. 11A: Systemic Administration of CCT020312 Improves Spatial Memory in P301S Mice: Time to Find the Platform.

The time to find the hidden platform in the Morris water maze test shortened in the group (grp) of wild type (WT) mice over the three successive testing days, reflecting a successive memorization of its location by the mice during the training period. Treatment with the drug did not change the learning curve in WT mice. P301S tau transgenic mice had a less steep learning curve, indicating reduced memorization capacity. P301S tau transgenic mice treated with the drug, however had a steeper learning curve than untreated P301S tau mice. Symbols indicate group means (N=8 per group). Error bars=standard error of the mean.

Figure 11B:
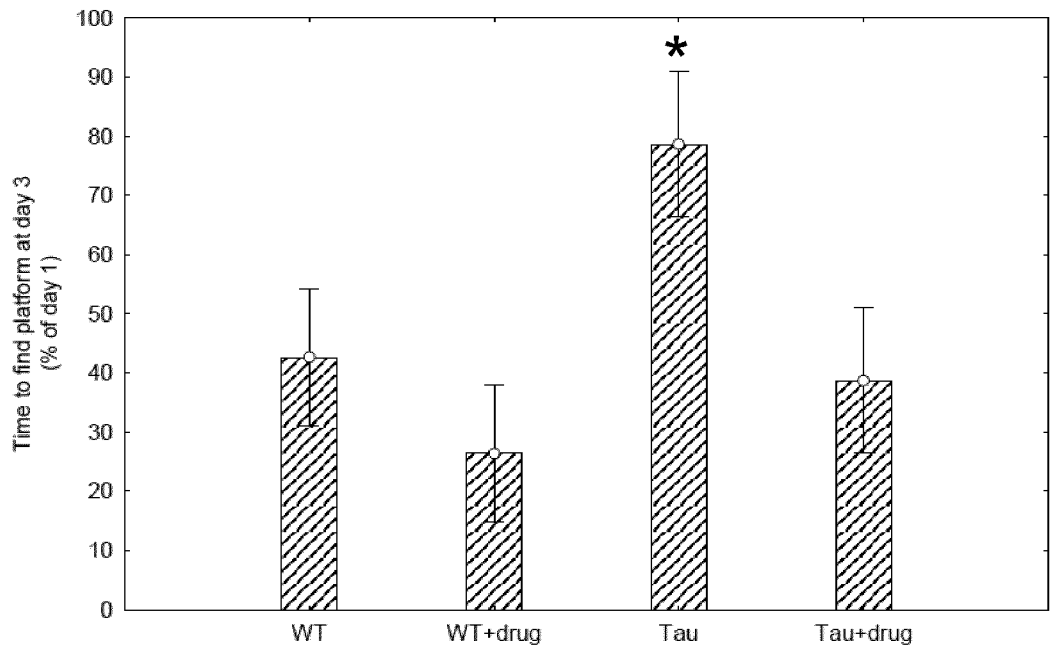

FIG. 11B: Systemic Administration of CCT020312 Improves Spatial Memory in P301S Mice: Quantification of Effects.

The learning efficacy in the mice to learn the Morris Water Maze task was expressed as the time to find the platform on the third day of learning, expressed as % of the time they required at day 1. WT=wild type mouse, drug=PERK activator CCT020312, tau=P301S tau mouse. Error bars=standard error of the mean. * P<0.05 vs. all other groups, ANOVA followed by post-hoc Bonferroni test.

Figure 11C:
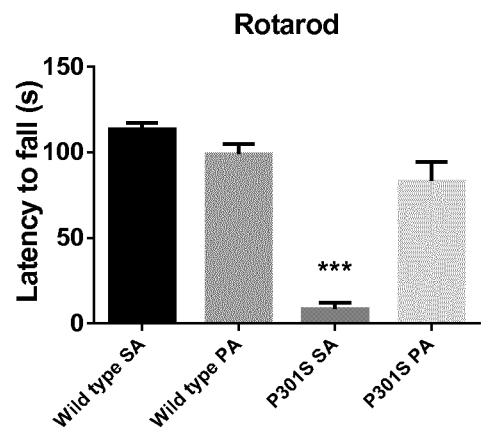

FIG. 11C: Systemic Administration of CCT020312 Improves Motor Deficit in P301S Mice Age matched wild type and P301S mice were injected intraperitoneally once daily for 6 weeks starting with the PERK activator (PA) CCT020312 (2 mg/kg) or saline (SA), until 23 weeks of age (n=12 for PA treated P301S mice, n=9 for other groups). In the Rotarod test, evaluating the balancing performance, SA-treated P301S mice performed significantly worse compared to all other groups. PA-treated P301S mice showed an increased performance compared to SA-treated P301S mice. One way ANOVA followed by post-hoc LSD test, *** P<0.001 vs. all other groups.

Figure 12:
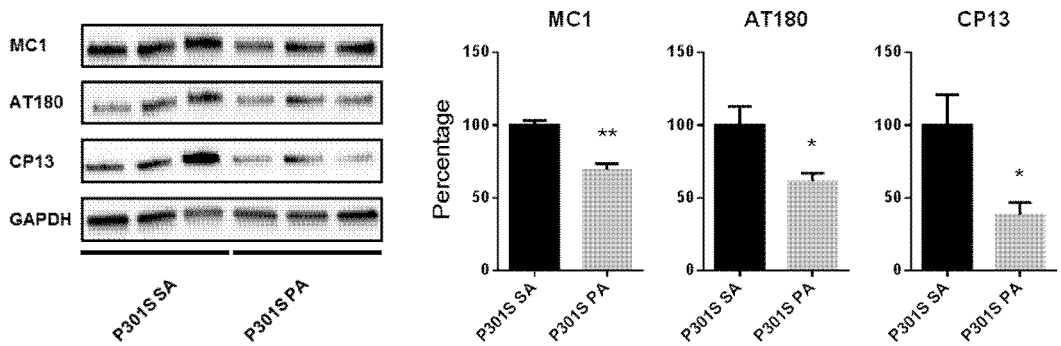

FIG. 12: Systemic Administration of CCT020312 Decreased Pathological Tau Species in P301S Mouse Brains.

P301S mice were injected intraperitoneally once daily for 6 weeks starting at 17 weeks of age with PERK activator CCT020312 (PA, 2 mg/kg) or saline (SA) (n=3 per group). Western blots of the soluble fraction of whole brain homogenates (left panel) were done with the antibodies MC1 (conformationally changed tau), AT180 (paired helical filament tau) and CP13 (S202-phosphorylated tau). GAPDH was used as loading control. Quantification of the blots (right panel, n=3 per group) and normalization to GAPDH demonstrated that PA-treatment decreased different tau species compared to SA treatment. t-Test, * P<0.05.

Figure 13:
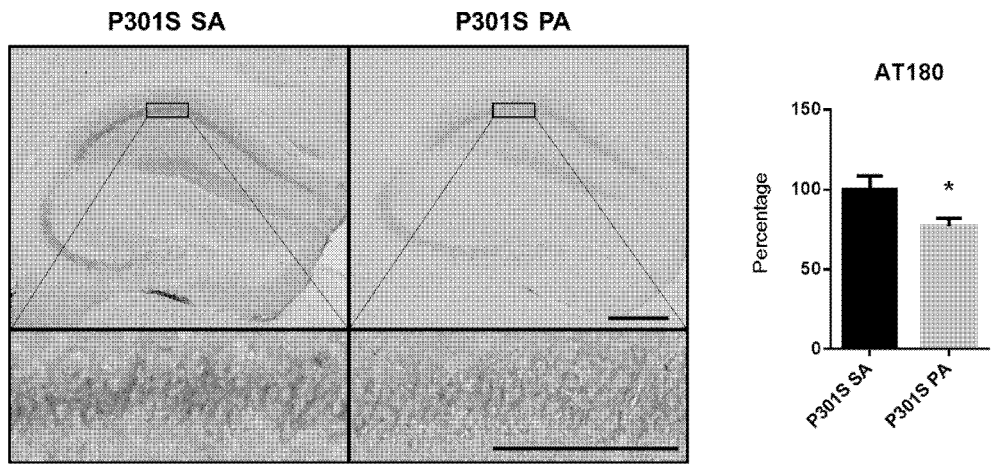

FIG. 13: Systemic Administration of CCT020312 Decreased the AT180-immunoreactivity in P301S Mouse Hippocampi.

P301S mice were injected intraperitoneally once daily for 6 weeks starting at 17 weeks of age with PERK activator CCT020312 (PA, 2 mg/kg) or saline (SA) (n=6 per group). Compared to saline-treated P301S mice (P301S SA), the immunoreactivity with the antibody AT180, raised against paired helical filament tau, was decreased in PA-treated P301S mice (P301S PA). The bar graph shows optical density of the CA1/CA2 and CA3 region from both groups. Upper scale bar=500 µm, lower scale bar=50 µm. t-Test, * P<0.05.

DETAILED DESCRIPTION OF THE INVENTION

As summarized before, the present invention relates to a compound functionally defined as a direct and/or indirect, preferably as a direct, PERK activator, a prodrug thereof, a derivative thereof and/or a pharmaceutically acceptable salt of any thereof, wherein the compound is for use in the treatment and/or prophylaxis of a tau-mediated neurodegenerative disease and/or of a tau-mediated neurodegenerative pathological condition, e.g. in higher mammals, particularly in humans. In contrast to the prior art, the invention relates to compounds acting on a kinase called PERK (protein kinase R-like endoplasmic reticulum kinase) as a new therapeutic approach to treat tauopathies.

Especially, the invention provides a new rational method to ameliorate symptoms and retard disease progression in tauopathies for treating and/or preventing tauopathies, i.e. primary and/or secondary tauopathies, especially in a patient population suffering from a neurodegenerative disease and/ or condition, which is at least partially, preferably predominantly, associated with abnormal phosphorylation, pathological conformational change, aggregation (i.e. oligomerization, polymerization, and fibrillization) and accumulation in the somatodendritic compartment of the axonal microtubule-associated protein tau.

Tauopathies are classified into primary and secondary tauopathies. The group of frontotemporal lobar degenerations (FTLD) is a heterogenous group defined by predominant atrophy of the frontal and temporal lobes of the brain. FTLDs comprise about 3-9% of dementia cases. About 40% of the FTLDs are primary tauopathies. Examples for primary tauopathy FTLDs are the disease entities Pick's disease (PiD), Corticobasal Degeneration (CBD), Argyrophilic Grain Disease (AGD), NFT-predominant dementia, and Progressive Supranuclear Palsy (PSP).

The most frequent secondary tauopathy is Alzheimer's disease (AD). It is the most frequent neurodegenerative disease. It accounts for about 40% of the dementia cases, and about 60-80% of the tauopathies. The neuropathological hallmark of AD is the extracellular aggregation of the protein amyloid beta, which is generally believed to be the primary event leading to a secondary intracellular accumulation of the microtubule-associated protein tau in the central nervous system.

All of these disorders are progressive in nature and lead to severe functional impairments, major individual and social burden, and ultimately death of the affected patient. For all these diseases, currently available therapeutic options are essentially limited to transient and incomplete symptomatic improvements. There is no approved disease-modifying, neuroprotective medical intervention available, which would allow retarding or ideally stopping the progression of the disorder, based on an intervention at the level of essential disease mechanisms, but there exists a huge clinical demand.

In particular, the invention relates to such a compound according as a direct and/or indirect PERK activator, wherein the compound is for use in the treatment and/or prophylaxis of a neurodegenerative disease and/or of a neurodegenerative pathological condition associated with and/or accompanied by tau aggregation, e.g. in higher mammals, particularly in humans.

The term "PERK" means protein kinase R-like endoplasmic reticulum kinase. The term "PERK activator" as used herein in relation to the invention means any compound or method to stimulate the kinase activity of PERK protein. In particular, the stimulation of the kinase activity of PERK protein, as determined by increased phosphorylation of its target proteins EIF2A and NRF2. Herein the term "EIF2A" means "eukaryotic translation initiation factor 2-alpha"; and the term "NRF2" means "nuclear factor erythroid 2-related factor 2". In the prior art, PERK commonly is nominated by one of the synonyms: EIF2AK3 (eukaryotic translation initiation factor 2-alpha kinase 3); PEK; or PERK; and is generally also known as PRKR-like endoplasmic reticulum kinase or protein kinase R (PKR)-like endoplasmic reticulum kinase.

PERK is an enzyme that is encoded by the EIF2AK3 gene in humans. In regard of its biological function, the protein encoded by this gene phosphorylates the alpha subunit of EIF2, leading to its inactivation, and thus to a rapid reduction of translational initiation and repression of global protein synthesis. It is a type I membrane protein located in the endoplasmic reticulum (ER), where it is induced by ER stress caused by misfolded proteins. In regard of its clinical significance it is known that patients with mutations in this gene develop Wolcott-Rallison syndrome (WRS). Known inhibitors of PERK are, for example, the compounds GSK2606414 and 3-Fluoro-GSK2606414. The rationale for using PERK inhibition in the prior art as therapeutic approach in neurodegenerative diseases is that PERK may be chronically overactive in these diseases, leading to a long-term harmful suppression of translation, being especially critical for synaptic proteins. Long-term PERK inhibition however also comes with serious consequences such as diabetes mellitus, liver and renal impairment, amongst others, resembling symptoms of Wolcott-Rallison Syndrome.

Wolcott-Rallison Syndrome is the clinical manifestation of a lack of function PERK, and is an autosomal recessive condition (i.e. mutations in the EIF2AK3 gene encoding PERK) with the symptoms of infancy-onset diabetes mellitus, multiple epiphyseal dysplasia, osteopenia, microcephaly, mental retardation or developmental delay and hepatic and renal dysfunction.

In the prior art, PERK signaling has been found to alleviate beta-amyloid associated neurotoxicity (Lee do et al. 2010) and reduce brainstem motoneuron death in a murine model of sleep apnea (Zhu et al. 2008), suggesting that PERK pathway activation could be a potential target for therapeutic fields other than cancer, including conditions of hypoxia-associated neurotoxicity and amyloid-beta-mediated neurodegeneration. However, in contrast to the present invention, no prior work has proposed to stimulate or activate PERK to treat tauopathies, i.e. neurodegenerative diseases induced by abnormal metabolization of the tau protein.

The inventors wish to emphasize that the term "neurodegenerative diseases" is very general to cover distinct disease entities characterized by progressive neuronal loss in defined regions of the central nervous system, caused by aberrant metabolism of specific aggregation-prone proteins. The individual disease entities (e.g. Parkinson's disease, Alzheimer's disease, PSP) are defined by the neuropathological and biochemical distinctions of the disease-causing proteins (e.g. alpha-synuclein, amyloid-beta, tau).

Since the molecular properties of these distinct proteins and the mechanisms by which they lead to neuronal dysfunction and degeneration are distinct (e.g. tau=intracellular aggregation, amyloid-beta=extracellular aggregation), it is the generally accepted concept that the distinct disease entities within the group of neurodegenerative diseases require distinct treatment approaches. Specifically, a therapeutic approach suggested to be effective to treat amyloid-beta induced neurodegeneration does by no means imply that the same approach is likely to be effective in tau-mediated neurodegeneration.

In the prior art, PERK is also known in the context of oncogenic cellular processes, for example, as described by Stockwell et al. 2012 and in relation hereto canonical PERK pathway was described as the underlying mechanism. In a tentative outlook, by this scientific article it was also proposed to stimulate PERK directly to treat neurodegenerative diseases, rather than to activate signaling cascades downstream of PERK. This work, however, studied diseases caused by abnormal metabolization of the protein amyloid-beta, but not, as is the case in the present invention, neurodegenerative diseases caused by abnormal metabolization of the tau protein, i.e. tauopathies and/or a neurodegenerative disease and/or condition, which is at least partially, preferably predominantly, associated with abnormal phosphorylation, pathological conformational change, aggregation (i.e. oligomerization, polymerization, and fibrillization) and accumulation in the somatodendritic compartment of the axonal microtubule-associated protein tau.

In contrast to the prior art addressing mainly PERK inhibition, or occasionally only the apoptotic arm of PERK of activation, the present invention pertains to the effects of indirect or direct PERK activation achieved via the neuroprotective arm of PERK activation.

Furthermore, neither Stockwell et al. 2012 nor any other publication in the prior art has provided any profound, and even not any initial data and evidence for likely motivating a skilled person to actually pursue any other therapeutic approach rather than PERK inhibition in attempts to treat tauopathies. In complete contrast to the invention, in the prior art there was a pronounced reluctance to even consider new therapeutic approaches in certain fields of treating and/or preventing tau-mediated neurodegenerative diseases and/or tau-mediated neurodegenerative pathological conditions, or neurodegenerative diseases associated with and/or accompanied by tau aggregation, and more particularly tauopathies. Also, in the prior art a dominant opinion was prevailing that tauopathies if anything should be treated by inhibition of PERK (van der Harg et al. 2014).

A genome wide association study (Hoglinger et al. 2011) confirmed the MAPT gene encoding tau protein and revealed three additional genes that influence the risk to develop PSP. One of these risk genes is EIF2AK3, encoding PERK. PERK is an integral part of the UPR. The UPR has been described to be affected in neurodegenerative diseases in general and in tauopathies in particular (Hetz et al. 2014).

Some articles describe that increasing the UPR activity (not specifically using PERK as target) is protective in neurodegenerative diseases (Loewen et al. 2010; Vaccaro et al. 2013). There are also descriptions that downstream events of PERK (but not PERK itself) are protective to cells (Cullinan et al. 2003; Bouman et al. 2011; B'Chir et al. 2013).

PERK inhibition or knockout were proposed as therapy in neurodegenerative diseases (not tau-related): Axten et al. 2012; Ma et al. 2013; Moreno et al. 2013; Pytel et al. 2014.

However, an increase of the PERK protein or activity, i.e. PERK activation, as a method to treat tauopathies and/or related tau-mediated neurodegenerative diseases and/or tau-mediated neurodegenerative conditions, as proposed by the present invention, has never been reported before in the prior art.

Indeed, in contrast to the prior art, the present inventors have found evidence for the first time that lack of PERK function is sufficient to induce changes reminiscent of early stages of various tau-mediated neurodegenerative diseases and/or conditions, confirming the importance of PERK in autophagy, which is implicated in a large number of neurodegenerative conditions, and thus in neurodegeneration (see Bruch et al. 2015).

The term "autophagy" relates to the basic catabolic mechanism that involves cell degradation of unnecessary or dysfunctional cellular components isolated from the rest of the cell within a double-membraned vesicle known as an autophagosome through the actions of lysosomes fused with the autophagosome. In the context of disease, autophagy is seen as an adaptive response to stress which promotes survival or in other cases to promote cell death and morbidity.

Any therapy of tau-mediated neurodegenerative diseases and/or tau-mediated neurodegenerative pathological conditions, which is based on PERK will therefore need to activate the positive aspects of PERK, such as autophagy and NRF2 and activating transcription factor 4 (ATF4) based neuroprotection, while avoiding overdrive to permanently suppress translation, or at least to cause long-term suppression of translation, or to activate apoptosis. Especially, the invention relates to a compound acting directly and/or indirectly, preferably directly, as a PERK activator, which is functionally characterized:

a) as a compound that stimulates the kinase activity of PERK protein and/or as a compound for use in method to stimulate the kinase activity of PERK protein;
b) preferably as a compound that stimulates the kinase activity of PERK protein and/or as a compound for use in method to stimulate the kinase activity of PERK protein; as determined by increased phosphorylation of its target proteins EIF2A and/or NRF2.

The skilled person is familiar with the identification (for example, the above mentioned LanthaScreen technology) and/or manufacture of the compounds, e.g. the PERK activator, related to the present invention. The skilled person is capable to select the appropriate manufacturing method depending on the selected compound, e.g. the selected PERK activator. For example, a compound of interest may be synthesized synthetically or semi-synthetically by chemical (organic) synthesis from appropriate precursors by means of known reaction patterns, and/or can be synthesized by means of complete or partial biotechnological processes. Of course chemical and biotechnological processes may be combined. Isolating, concentrating and/or purifying follow methods known in the art.

Preferably, the compound according to the invention is a direct and/or indirect PERK activator, a prodrug thereof, a derivative thereof and/or a pharmaceutically acceptable salt of any thereof, for use in the treatment and/or prophylaxis of a neurodegenerative disease and/or of a neurodegenerative pathological condition, wherein the neurodegenerative disease is at least one tauopathy and/or a neurodegenerative pathological condition associated with at least one hallmark (a characteristic sign and/or characteristic symptom) of a tauopathy; preferably at least one tauopathy selected from the group consisting of 3R-tauopathy, 4R-tauopathy, and mixed 3R-/4R-tauopathy. The tauopathy, e.g. the 3R-tauopathy, 4R-tauopathy, and mixed 3R-/4R-tauopathy, may be a primary tauopathy, that is for example, the sole and/or the predominant pathology of the neurodegenerative disease and/or neurodegenerative pathological condition; or the tauopathy, e.g. the 3R-tauopathy, 4R-tauopathy, and mixed 3R-/4R-tauopathy, may be a secondary tauopathy, that is for example, a concomitant pathology of the neurodegenerative disease and/or neurodegenerative pathological condition.

The term primary tauopathy refers to diseases where tau accumulation is the sole or predominant intracerebral protein accumulation. The term secondary tauopathy refers to diseases where tau accumulation is concomitant to intracerebral accumulation of other proteins termed amyloidogenic (e.g. amyloid-beta in Alzheimer's disease).

The terms "tauopathy", "tauopathies", "tauopathic" and similar terms as used herein in relation to the invention define a class of neurodegenerative diseases, i.e. primary and/or secondary tauopathies, which are at least partially, preferably predominantly, associated with abnormal phosphorylation, pathological conformational change, aggregation (i.e. oligomerization, polymerization, and fibrillization) and accumulation in the somatodendritic compartment of the axonal microtubule-associated protein tau. Particularly, the terms define neurodegenerative diseases and/or neurodegenerative conditions associated with abnormal intracellular accumulation of the microtubule associated protein tau in the human nervous system.

The tau protein is encoded by the MAPT gene on chromosome 17. It is translated into mainly 6 tau protein isoforms. Tau isoforms containing either three or four microtubule binding domains (three repeats=3R, four repeats=4R) as result of alternative splicing of exon 10 of the MAPT gene. The terms "3R-tauopathy", "3R-tauopathies", "3R-tauopathic", "3R-tau" and similar terms are commonly understood as a class of neurodegenerative diseases associated with abnormal intracellular accumulations in the human nervous system of tau protein, preferentially of 3R-tau isoforms. The terms "4R-tauopathy", "4R-tauopathies", "4R-tauopathic", "4R-tau" and similar terms as used herein mean a class of neurodegenerative diseases associated with abnormal intracellular accumulations in the human nervous system of 4R-tau protein.

Thus, the terms "3R-tauopathy", "3R-tauopathies", "3R-tauopathic", "3R-tau" and similar terms as used herein in relation to the invention mean a class of neurodegenerative diseases associated with abnormal intracellular accumulations in the human nervous system of tau protein, preferentially of tau isoforms containing three microtubule binding domains (MBD), resulting by alternative splicing of exon 10 of the MAPT gene; 3R means three repeats. The 3R-isoforms differ from the 4R-isoforms in the absence of a fourth 31-amino acid repeat coded by exon 10.

The terms "4R-tauopathy", "4R-tauopathies", "4R-tauopathic", "4R-tau" and similar terms as used herein in relation to the invention mean a class of neurodegenerative diseases associated with abnormal intracellular accumulations in the human nervous system of tau protein, preferentially of tau isoforms containing four MBDs resulting by alternative splicing of exon 10 of the MAPT gene; 4R means four repeats. The 4R-isoforms differ from the 3R-isoforms in the presence of a fourth 31-amino acid repeat coded by exon 10.

Thus, in one aspect the invention is characterized in that the said compound is for use in the treatment and/or prophylaxis of a neurodegenerative disease and/or of a neurodegenerative pathological condition, e.g. in higher mammals, particularly in humans, wherein the neurodegenerative disease is at least one tauopathy and/or a neurodegenerative pathological condition associated with at least one hallmark of a tauopathy, where tauopathy may be the sole, the predominant or a concomitant pathology; and wherein at least one tauopathy is a form of 3R-tauopathy, 4R-tauopathy, or mixed 3R-/4R-tauopathy, and that is a) associated with a disease selected from the group consisting of
   i. diseases where tauopathy is the sole or predominant pathology, including, but not limited to, Progressive Supranuclear Palsy (PSP), Argyrophilic Grain Disease (AGD), Corticobasal Degeneration (CBD), Frontotemporal lobar degeneration with tau aggregation (FTLD-tau; sporadic or caused by MAPT mutations), Pick's disease (PiD), Tangle-predominant dementia, Guadeloupe-Parkinson Dementia Complex, Guam-Parkinson Dementia Complex (Lytico-Bodig disease), Dementia pugilistica (chronic traumatic encephalopathy), Progressive subcortical gliosis; preferably, wherein the disease is selected from the group consisting of the diseases listed here under i.;
   ii. diseases where tauopathy is a characteristic concomitant co-pathology, including, but not limited to Alzheimer's disease (AD), Huntington's disease (HD), Parkinson's disease (PD), Multiple System Atrophy (MSA), Motor neuron disease (MND) with neurofibrillary tangles, Hallervorden-Spatz disease (HSD), Creutzfeldt-Jakob disease (CJD), Gerstmann-Sträussler-Scheinker Disease, Niemann-Pick Disease Type C, Lead encephalopathy, Myotonic dystrophy, Prion protein cerebral amyloid angiopathy, Postencephalitic parkinsonism, Subacute sclerosing panencephalitis (SSPE), Tuberous sclerosis, Down's syndrome; preferably, wherein the disease is selected from the group consisting of the diseases listed here under ii.;

or preferably that is b) associated with a disease selected from the group consisting of Progressive Supranuclear Palsy (PSP), Corticobasal Degeneration (CBD), Argyrophilic Grain Disease (AGD), Pick's disease (PiD), Frontotemporal lobar degeneration with tau aggregation (FTLD-tau; sporadic or caused by MAPT mutations), Tangle-predominant dementia, Guadeloupe-Parkinson Dementia Complex, Guam-Parkinson Dementia Complex (Lytico-Bodig disease), Dementia pugilistica (chronic traumatic encephalopathy), Progressive subcortical gliosis, and any combination thereof;

or more preferably that is c) a disease selected from the group consisting of Progressive Supranuclear Palsy (PSP), Corticobasal Degeneration (CBD), Argyrophilic Grain Disease (AGD), Pick's disease (PiD), Frontotemporal lobar degeneration with tau aggregation (FTLD-tau; sporadic or caused by MAPT mutations), Tangle-predominant dementia, Guadeloupe-Parkinson Dementia Complex, Guam-Parkinson Dementia Complex (Lytico-Bodig disease), Dementia pugilistica (chronic traumatic encephalopathy), Progressive subcortical gliosis, and any combination thereof.

The present invention also relates to pharmaceutical compositions. In one aspect, the invention relates to a pharmaceutical composition comprising a compound acting as a direct and/or indirect PERK activator, a prodrug thereof, a derivative thereof and/or a pharmaceutically acceptable salt of any thereof, as defined according to the invention, together with at least one pharmaceutically acceptable component selected from the group consisting of excipients, additives and/or auxiliaries. The said compound as defined according to the invention as indicated herein.

In another aspect, the invention relates to a pharmaceutical composition comprising a compound acting as a direct and/or indirect PERK activator, a prodrug thereof, a derivative thereof and/or a pharmaceutically acceptable salt of any thereof, for use in the treatment and/or prophylaxis of a tau-mediated neurodegenerative disease and/or of a tau-mediated neurodegenerative pathological condition, e.g. in higher mammals, particularly in humans. The said compound as defined according to the invention as indicated herein.

In particular, the pharmaceutical composition according to the invention is characterized in that the compound as defined according to the invention is for use in the treatment and/or prophylaxis of a neurodegenerative disease and/or of a neurodegenerative pathological condition associated with and/or accompanied by tau aggregation.

The skilled person is familiar with the manufacture of a pharmaceutical composition comprising the compounds, e.g. the PERK activator, related to the present invention. The skilled person is capable to select the appropriate manufacturing method for a pharmaceutical composition depending on the selected compound, e.g. the selected PERK activator and/or the mode of administration of choice. For example, the pharmaceutical composition may be an enteral or parenteral pharmaceutical formulation. The pharmaceutical composition may be, for example but not limited to, for oral, rectal, transdermal, intraperitoneal, subcutaneous, intrapulmonary, intravenous, or intrathecal use. The PERK activator compound and its pharmaceutical composition according to the present invention preferably enables the crossing of a sufficiently therapeutically active amount of the PERK activator across the blood brain barrier and/or may be administered directly into or adjacent to the liquor of the central nervous system. An example is injection adjacent to or into spinal cord. The manufacture of pharmaceutical compositions comprising the compounds, e.g. the PERK activator, related to the present invention is selected by the skilled person according to the means of known formulation methods as well as selecting appropriate and commonly known excipients, additives and/or auxiliaries, depending on the choice of the selected compound and selected mode of administration.

Preferably, the pharmaceutical composition according to the invention is for use in the treatment and/or prophylaxis of a neurodegenerative disease and/or of a neurodegenerative pathological condition, e.g. in higher mammals, particularly in humans, wherein the neurodegenerative disease is selected from the group consisting of:

a) at least one tauopathy and/or a neurodegenerative pathological condition associated with at least one hallmark of a tauopathy; preferably at least one tauopathy selected from the group consisting of 3R-tauopathy, 4R-tauopathy, and mixed 3R/4R-tauopathy;

b) at least one tauopathy in a form of 3R-tauopathy, 4R-tauopathy, or mixed 3R-/4R-tauopathy, and that are i. diseases where tauopathy is the sole or predominant pathology, including, but not limited to Progressive Supranuclear Palsy (PSP), Argyrophilic Grain Disease (AGD), Corticobasal Degeneration (CBD), Frontotemporal lobar degeneration with tau aggregation (FTLD-tau; sporadic or caused by MAPT mutations), Pick's disease (PiD), Tangle-predominant dementia, Guadeloupe-Parkinson Dementia Complex, Guam-Parkinson Dementia Complex (Lytico-Bodig disease), Dementia pugilistica (chronic traumatic encephalopathy), Progressive subcortical gliosis; preferably, wherein the disease is selected from the group consisting of the diseases listed here under i.;

ii. diseases where tauopathy is a characteristic concomitant co-pathology, including, but not limited to Alzheimer's disease (AD), Huntington's disease (HD), Parkinson's disease (PD), Multiple System Atrophy (MSA), Motor neuron disease (MND) with neurofibrillary tangles, Hallervorden-Spatz disease (HSD), Creutzfeldt-Jakob disease (CJD), Gerstmann-Sträussler-Scheinker Disease, Niemann-Pick Disease Type C, Lead encephalopathy, Myotonic dystrophy, Prion protein cerebral amyloid angiopathy, Postencephalitic parkinsonism, Subacute sclerosing panencephalitis (SSPE), Tuberous sclerosis, Down's syndrome; preferably, wherein the disease is selected from the group consisting of the diseases listed here under ii.;

and preferably c) at least one tauopathy in a form of 3R-tauopathy, 4R-tauopathy, or mixed 3R-/4R-tauopathy, and that is associated with a disease selected from the group consisting of Progressive Supranuclear Palsy (PSP), Corticobasal Degeneration (CBD), Argyrophilic Grain Disease (AGD), Pick's disease (PiD), Frontotemporal lobar degeneration with tau aggregation (FTLD-tau; sporadic or caused by MAPT mutations), Tangle-predominant dementia, Guadeloupe-Parkinson Dementia Complex, Guam-Parkinson Dementia Complex (Lytico-Bodig disease), Dementia pugilistica (chronic traumatic encephalopathy), Progressive subcortical gliosis and any combination thereof;
and more preferably
d) at least one tauopathy in a form of 3R-tauopathy, 4R-tauopathy, or mixed 3R-/4R-tauopathy, and that is a disease selected from the group consisting of Progressive Supranuclear Palsy (PSP), Corticobasal Degeneration (CBD), Argyrophilic Grain Disease (AGD), Pick's disease (PiD), Frontotemporal lobar degeneration with tau aggregation (FTLD-tau; sporadic or caused by MAPT mutations), Tangle-predominant dementia, Guadeloupe-Parkinson Dementia Complex, Guam-Parkinson Dementia Complex (Lytico-Bodig disease), Dementia pugilistica (chronic traumatic encephalopathy), Progressive subcortical gliosis and any combination thereof.

The pharmaceutical composition according to the invention can comprise a compound as defined herein in the context of the invention as a direct and/or indirect, preferably a direct, PERK activator, a prodrug thereof, a derivative thereof and/or a pharmaceutically acceptable salt of any thereof, together with at least one pharmaceutically acceptable component selected from the group consisting of excipients, additives and/or auxiliaries.

Figure 1:
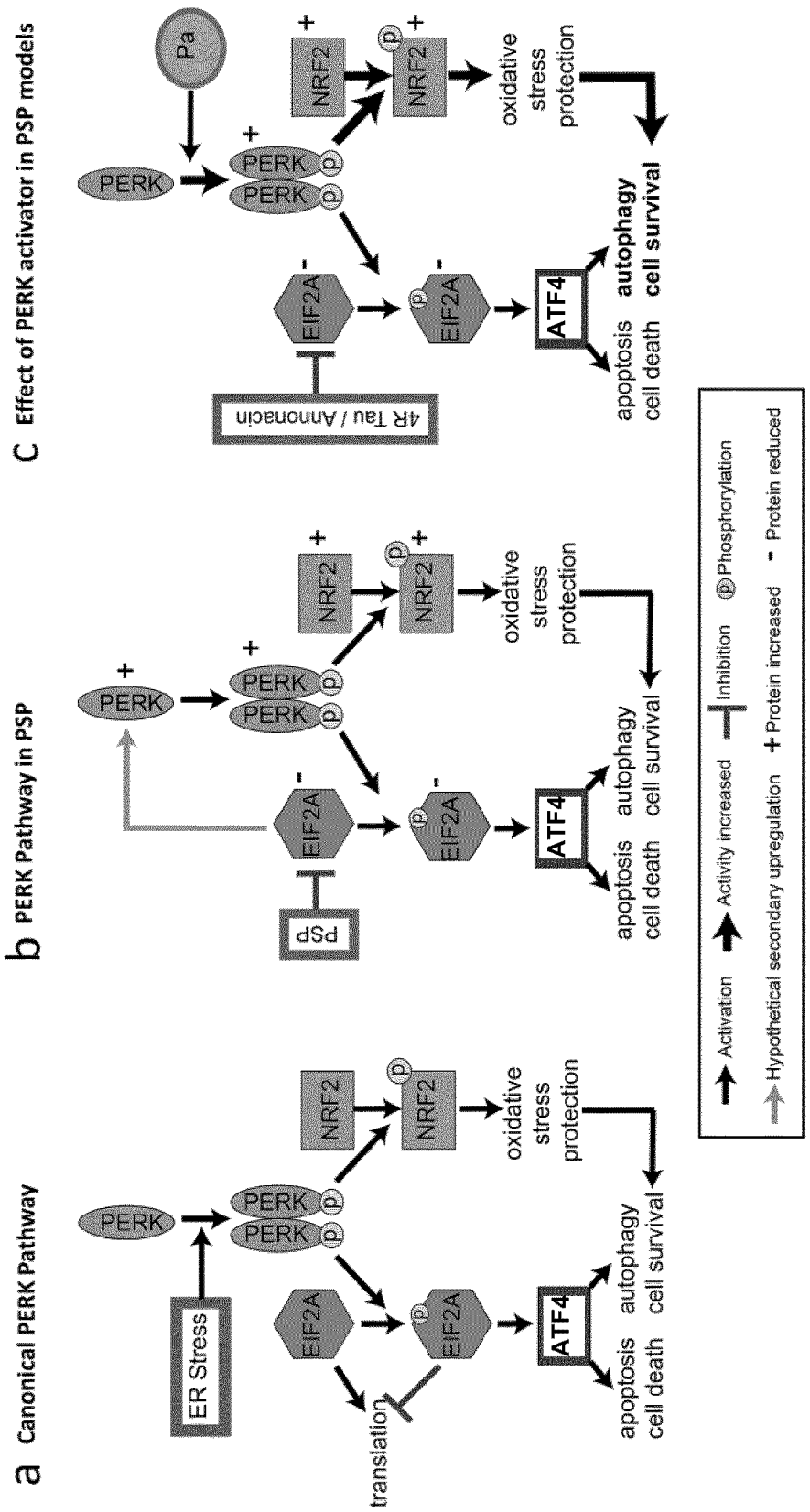
FIG. 1: PERK Signaling
a) The canonical PERK pathway. An overload of misfolded proteins in the endoplasmic reticulum (ER stress) induces activation of PERK by autophosphorylation (p). pPERK phosphorylates EIF2A and NRF2. pEIF2A leads to global suppression of translation and induces the activating transcription factor 4 (ATF4). Depending on the cellular context, ATF4 regulated transcription may either induce apoptotic cell death or autophagy and cell survival. pNRF2 induces mechanisms protecting against oxidative stress and promoting cell survival.

The finding and evidence of the present invention related to direct and/or indirect, preferably direct, PERK activators provides a unique and broadly applicable opportunity for a valuable novel treatment and/or prophylaxis of tau-mediated neurodegenerative diseases and/or of tau-mediated neurodegenerative pathological conditions. The broad applicability of the invention is based on the unique finding and data generated by the inventors for the first time with the representative PERK activating compound CCT020312, suggesting that any compound functionally defined as a direct and/or indirect, preferably direct, PERK activator should be suitable for the treatment and/or prophylaxis of the present invention. The PERK activating compound CCT020312 is the very first selective PERK activating compound that became known to the public, functionally and also structurally, and thus served the inventors as a general representative for compound classes characterized functionally as PERK activators. Therefore, the surprising finding of the present invention, as shown and supported by the experimental data and evidence provided by the inventors herein for the first time, when using the representative PERK activating compound CCT020312 is broadly applicable to each and any PERK activating compound class. Reference is made to FIG. 1, which is contrasting the classical canonical pathway (A) vs. the unique finding of the present invention pertaining to PERK activating compounds, i.e. the PERK pathway in the prototypical tauopathy PSP (B) and the changes induced by the PERK activator in cell models of tauopathies (C).

According to the present invention, the PERK activating compound is comprising a substituted saturated or partially unsaturated 5-membered heteroalicyclic ring or a substituted 5-membered heteroaryl ring, and preferably is a substituted partially unsaturated 5-membered heteroalicyclic ring; of formula (I),

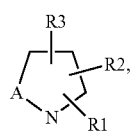

(I)

wherein N denotes nitrogen (N), and A denotes a heteroatom, preferably nitrogen (N) or oxygen (O), more preferably nitrogen (N);

wherein the substituent R1 is a phenyl or benzyl group which is mono- or di-substituted with halogen or with partially or fully halogenated $C_1$-$C_2$ alkyl groups, wherein the halogenated C1-C2 alkyl group preferably is a mono-, di- or tri-substituted halogen methyl group; or R1 is a piperidinyl group, preferably a piperidin-4-yl group, which can optionally be N-substituted with a $C_1$-$C_3$ alkyl group which may be further substituted with R6 as defined herein below;

wherein the substituent R2 is an optionally branched $C_1$-$C_3$ alkyl group, a R4, $(R5)_n$-B—$(CH_2)_m$—C=O group, wherein R4 and R5 independently from each other denote an optionally branched $C_1$-$C_3$ alkyl group, B is nitrogen or oxygen, and n is 0 if B is oxygen or n is 1 if B is nitrogen, and m is an integer from 0 to 4, and preferably m is an integer from 0 to 2;

wherein the substituent R3 is oxo; or R3 means R6; or R3 means R6 which is linked to the ring of formula (I) by a $C_1$-$C_3$ alkylene group or $C_1$-$C_3$ alkylene oxy group;

wherein R6 is a substituted or unsubstituted heteroaryl ring selected from the group consisting of quinoline, isoquinoline, 4H-pyrido[1,2-α]pyrimidine, indole, isoindole, and a substituted or unsubstituted naphthalene ring, and wherein the heteroaryl or naphthalene ring can carry an oxo group; and wherein the optional substituents of R6 can be halogen, carboxyl, and/or a phenyl or benzyl group, wherein optionally the phenyl or benzyl group may be mono- or di-substituted with halogen or with partially or fully halogenated $C_1$-$C_2$ alkyl groups, wherein the halogenated $C_1$-$C_2$ alkyl group preferably is a mono-, di- or tri-substituted halogen methyl group;

or wherein the substituents R2 and R3, if A is oxygen (O), combine with each other to a —CH=CH—CH=CH— group which anneals with an unsaturated 5-membered heterocyclic ring in the formula (I) to form a bicyclic 9-membered heteroaryl ring which optionally may be mono- or di-substituted with halogen or with partially or fully halogenated $C_1$-$C_2$ alkyl groups, wherein the halogenated $C_1$-$C_2$ alkyl group preferably is a mono-, di- or tri-substituted halogen methyl group; preferably wherein the bicyclic 9-membered heteroaryl ring is mono- or di-substituted with halogen.

Preferably, according to the present invention, the PERK activating compound is comprising a substituted saturated or partially unsaturated 5-membered heteroalicyclic ring or a substituted 5-membered heteroaryl ring, and preferably is a substituted partially unsaturated 5-membered heteroalicyclic ring; of the above formula (I), wherein N denotes nitrogen (N), and A denotes nitrogen (N) or oxygen (O), preferably nitrogen (N);

wherein the substituent R1 is a phenyl or benzyl group which is mono- or di-substituted with halogen or with partially or fully halogenated $C_1$-$C_2$ alkyl groups, wherein the halogenated C1-C2 alkyl group preferably is a mono-, di- or tri-substituted halogen methyl group;

wherein the substituent R2 is an optionally branched $C_1$-$C_3$ alkyl group, a R4, $(R5)_n$-B—$(CH_2)_m$—C=O group, wherein R4 and R5 independently from each other denote an optionally branched $C_1$-$C_3$ alkyl group, B is nitrogen or oxygen, and n is 0 if B is oxygen or n is 1 if B is nitrogen, and m is an integer from 0 to 4, and preferably m is an integer from 0 to 2;

wherein the substituent R3 is oxo; or R3 means R6; or R3 means R6 which is linked to the ring of formula (I) by a $C_1$-$C_3$ alkylene group or $C_1$-$C_3$ alkylene oxy group;

wherein R6 is a substituted or unsubstituted heteroaryl ring selected from the group consisting of quinoline, isoquinoline, indole, isoindole, and a substituted or unsubstituted naphthalene ring, wherein the heteroaryl or naphthalene ring can carry an oxo group; and wherein the optional substituents of R6 can be halogen, carboxyl, and/or a phenyl or benzyl group, wherein optionally the phenyl or benzyl group may be mono- or di-substituted with halogen or with partially or fully halogenated $C_1$-$C_2$ alkyl groups, wherein the halogenated $C_1$-$C_2$ alkyl group preferably is a mono-, di- or tri-substituted halogen methyl group.

The term "ene" as used as a suffix herein as part of a group denotes a bivalent radical at the two terminal ends of the group. For example, a $C_1$-$C_3$ alkylene group denotes a bivalent alkyl group such as methylene (—$CH_2$—), ethylene (—$CH_2CH_2$—), or propylene (—$CH_2CH_2CH_2$—). If term "ene" is used as a suffix in the $C_1$-$C_3$ alkylene oxy group, then it denotes a bivalent alkyloxy group such as methylene oxy (—$CH_2O$—), ethylene oxy (—$CH_2CH_2O$—), or propylene oxy (—$CH_2CH_2CH_2O$—); the methylene oxy (—$CH_2O$—) group is the preferred bivalent alkyloxy group.

Within the compounds of the present invention according to the above formula (I) preferably the following meanings are applicable; "optionally branched $C_1$-$C_3$ alkyl group" preferably means one of methyl, ethyl, propyl, isopropyl group; "substituted ring of formula (I)" more preferably means one of substituted pyrazole ring, substituted isoxazole ring, substituted dihydropyrazole ring, or substituted pyrazolidine ring, and even more preferably a substituted dihydropyrazole ring or a substituted isoxazole ring; "halogen means one of fluor, chlorine, and/or bromine.

After the invention was made, some further PERK activating compounds were disclosed in the scientific literature, but without any reference to tauopathy; see Xie et al. 2015. The authors of this article refer to diseases like cancer, diabetes, (likely beta-amyloid-pathology in) Alzheimer's disease, and in particular COPD (chronic obstructive pulmonary disease). But they do neither address nor realize any tau-mediated neurodegenerative disease and/or neurodegenerative condition, which in contrast are at the heart of the present invention.

Suitable compound classes acting as PERK activators are preferably derived from the group consisting of dihydropyrazol compounds and/or isoxazol compounds, a prodrug thereof, a derivative thereof and/or a pharmaceutically acceptable salt of any thereof; more preferably the compounds are derived from the dihydropyrazol compound class.

In still a further aspect, the compounds according to the invention, or the pharmaceutical composition according to the invention, each independently are characterized in that the compound acting as a direct and/or indirect PERK activator is selected from the group consisting of dihydropyrazol compounds, a prodrug thereof, a derivative thereof and/or a pharmaceutically acceptable salt of any thereof, characterized in that the dihydropyrazol compound acts as an activator of PERK, and preferably increases the phosphorylation of EIF2A and/or NRF2. Especially, in this aspect of the present invention the dihydropyrazol compound acting as an activator of PERK preferably does not inhibit the activity of cyclin dependent kinases.

In a representative embodiment of the present invention the compound defined according to the invention or the pharmaceutical composition according to the invention, is characterized in that the compound acting as a PERK activator is selected from the group consisting of 6-bromo-3-[5-(4-bromo-phenyl)-1-(3-diethylamino-propionyl)-4,5-dihydro-1H-pyrazol-3-yl]-4-phenyl-1H-quinolin-2-one (PERK activator CCT020312) and ethyl 2-(3,5-bis(trifluoromethyl)phenyl)-3-oxo-2,3-dihydro-1H-pyrazole-4-carboxylate, a prodrug thereof, a derivative thereof and/or a pharmaceutically acceptable salt of any thereof.

In still a further aspect, the compounds according to the invention, or the pharmaceutical composition according to the invention, each independently are characterized in that the compound acting as a direct and/or indirect PERK activator is selected from the group consisting of isoxazol compounds, a prodrug thereof, a derivative thereof and/or a pharmaceutically acceptable salt of any thereof, characterized in that the isoxazol compound acts as an activator of PERK, and preferably increases the phosphorylation of EIF2A and/or NRF2. In a representative embodiment of the present invention the compound defined according to the invention or the pharmaceutical composition according to the invention, is characterized in that the compound acting as a PERK activator is 5-(6-((3-(2,6-dichlorophenyl)-5-isopropylisoxazol-4-yl)methoxy)naphthalen-2-yl)-2-fluorobenzoic acid, a prodrug thereof, a derivative thereof and/or a pharmaceutically acceptable salt of any thereof.

A further suitable compound class acting as PERK activators is derived from the group consisting of substituted ureido compounds, a prodrug thereof, a derivative thereof and/or a pharmaceutically acceptable salt of any thereof. A representative of this compound class is 2-(4-(2-(1-(2,4-bis(trifluoromethyl)benzyl)-3-(4-((trifluoromethyl)thio)phenyl)ureido)ethyl)phenoxy)-2-methylpropanoic acid. Further PERK activators described in the literature are: Tauroursodeoxycholic acid (Gani et al. 2015), Palmitic acid (Win et al. 2015), Metformin (Moon et al. 2015), Olanzapine and Risperidone (Ozasa et al. 2013), Phenformin (Yang et al. 2013), Resveratrol (Yan et al. 2010) and Salvianolic acid (Wu et al. 2009). Risperidone is chemically named 3-[2-[4-[6-fluoro-1,2-benzisoxazole-3-yl]-1-piperidinyl]ethyl]-6,7,8,9-tetrahydro-2-methyl-4H-pyrido[1,2-α]pyrimidin-4-one.

The representative PERK activator CCT020312 as used in the present invention is available from Merck Millipore or can be synthesized by methods known to the skilled person.

The present invention also comprises a method for the treatment and/or prophylaxis in a patient having a tau-mediated neurodegenerative disease and/or of a tau-mediated neurodegenerative pathological condition, e.g. in higher mammals, particularly in humans; preferably of a neurodegenerative disease and/or of a neurodegenerative pathological condition associated with and/or accompanied by tau aggregation; said method comprising administering to the patient a pharmacologically effective amount of a compound acting as a direct and/or indirect PERK activator, a prodrug thereof, a derivative thereof and/or a pharmaceutically acceptable salt of any thereof.

The method for the treatment and/or prophylaxis according to the invention is preferably characterized in that the said method comprises administering to the patient a pharmacologically effective amount of a compound as defined herein according to any aspect of the invention, or a pharmaceutical composition according to any aspect of the invention.

Particularly, the method for the treatment and/or prophylaxis according to the invention is characterized in that the compound is for use in the treatment and/or prophylaxis of a neurodegenerative disease and/or of a neurodegenerative pathological condition, e.g. in higher mammals, particularly in humans, wherein the neurodegenerative disease is selected from the group consisting of:
a) at least one tauopathy and/or a neurodegenerative pathological condition associated with at least one hallmark of a tauopathy; preferably at least one tauopathy selected from the group consisting of 3R-tauopathy, 4R-tauopathy, mixed 3R-/4R-tauopathy,
b) at least one tauopathy in a form of 3R-tauopathy, 4R-tauopathy, or mixed 3R-/4R-tauopathy, and that is associated with:
  i. diseases where tauopathy is the sole or predominant pathology, including, but not limited to Progressive Supranuclear Palsy (PSP), Argyrophilic Grain Disease (AGD), Corticobasal Degeneration (CBD), Frontotemporal lobar degeneration with tau aggregation (FTLD-tau; sporadic or caused by MAPT mutations), Pick's disease (PiD), Tangle-predominant dementia, Guadeloupe-Parkinson Dementia Complex, Guam-Parkinson Dementia Complex (Lytico-Bodig disease), Dementia pugilistica (chronic traumatic encephalopathy), Progressive subcortical gliosis; preferably, wherein the disease is selected from the group consisting of the diseases listed here under i.;
  ii. diseases where tauopathy is a characteristic concomitant co-pathology, including, but not limited to Alzheimer's disease (AD), Huntington's disease (HD), Parkinson's disease (PD), Multiple System Atrophy (MSA), Motor neuron disease (MND) with neurofibrillary tangles, Hallervorden-Spatz disease (HSD), Creutzfeldt-Jakob disease (CJD), Gerstmann-Sträussler-Scheinker Disease, Niemann-Pick Disease Type C, Lead encephalopathy, Myotonic dystrophy, Prion protein cerebral amyloid angiopathy, Postencephalitic parkinsonism, Subacute sclerosing panencephalitis (SSPE), Tuberous sclerosis, Down's syndrome; preferably, wherein the disease is selected from the group consisting of the diseases listed here under ii.;
and preferably
c) at least one tauopathy in a form of 3R-tauopathy, 4R-tauopathy, or mixed 3R-/4R-tauopathy, and that is associated with:
  a disease selected from the group consisting of Progressive Supranuclear Palsy (PSP), Corticobasal Degeneration (CBD), Argyrophilic Grain Disease (AGD), Pick's disease (PiD), Frontotemporal lobar degeneration with tau aggregation (FTLD-tau; sporadic or caused by MAPT mutations), Tangle-predominant dementia, Guadeloupe-Parkinson Dementia Complex, Guam-Parkinson Dementia Complex (Lytico-Bodig disease), Dementia pugilistica (chronic traumatic encephalopathy), Progressive subcortical gliosis and any combination thereof;
and more preferably
d) at least one tauopathy in a form of 3R-tauopathy, 4R-tauopathy, or mixed 3R-/4R-tauopathy, and that is a disease selected from the group consisting of Progressive Supranuclear Palsy (PSP), Corticobasal Degeneration (CBD), Argyrophilic Grain Disease (AGD), Pick's disease (PiD), Frontotemporal lobar degeneration with tau aggregation (FTLD-tau; sporadic or caused by MAPT mutations), Tangle-predominant dementia, Guadeloupe-Parkinson Dementia Complex, Guam-Parkinson Dementia Complex (Lytico-Bodig disease), Dementia pugilistica (chronic traumatic encephalopathy), Progressive subcortical gliosis and any combination thereof.

The invention provides significant advantages over the state of the art related to the treatment and/or prophylaxis of neurodegenerative diseases like tauopathies, or other neurodegenerative diseases where tauopathy is, for example, the sole or predominant pathology or, for example, where tauopathy is a characteristic concomitant co-pathology.

In still another aspect of the invention the compounds acting as a direct and/or indirect PERK activator, a prodrug thereof, a derivative thereof and/or a pharmaceutically acceptable salt of any thereof, the pharmaceutical compositions comprising said compound defined according to the invention, or the methods of treatment and/or prophylaxis, each independently are characterized in that the compound as defined herein according to the invention is for adjuvant use in the treatment and/or prophylaxis of a neurodegenerative disease and/or of a neurodegenerative pathological condition other than tauopathy, especially other than 4R-tauopathy, and which other neurodegenerative disease and/or other neurodegenerative pathological condition have a different underlying cause of the disease than tauopathy, especially which have a different underlying cause of the disease than 4R-tauopathy. For example, the PERK activator according to the present invention, or pharmaceutical compositions therewith, can be used in the adjuvant treatment or prophylaxis of other neurodegenerative diseases, e.g., caused by aggregation of amyloidogenic proteins, including, but not limited to alpha-synuclein, amyloid-beta, prion protein, huntingtin, TAR DNA-binding protein 43, or Fused in Sarcoma protein.

The novel use of a PERK activator according to the present invention provides a unique opportunity to alleviate the reluctant behavior in the prior art for searching potentially successful alternative medical treatment approaches with regard to tauopathies. Especially for rare tauopathic indications, e.g. like PSP, the treatment and/or prophylaxis according to the invention with a PERK activator may pave the way for new medications with efficacy and disease progression modifying potential. Neurodegenerative diseases which next to a tauopathy, for example, besides a 4R-tauopathy, have further causes, the treatment and/or prophylaxis with PERK activators may at least provide a unique opportunity for use as adjuvant therapy. Thus, the invention makes available novel opportunities for compounds in clinical use in patients suffering from tauopathies and other neurodegenerative diseases caused by aggregation of amyloidogenic proteins to ameliorate symptoms or delay or halt disease progression. The few past methodological approaches aiming at neuroprotective treatment of tauopathies failed to meet predefined criteria for efficacy in clinical trials (e.g. Tolosa et al., 2014; Boxer et al., 2014). Therefore, completely new conceptual approaches are required, and the present invention describes a new and surprising molecular approach.

Further Exemplification of the Invention

There are variable possibilities to advantageously develop, and develop further, the teaching of the present invention. For this purpose, reference is made to the examples below, which describe the invention in a representative way.

In the Examples we present an in vitro study describing the state of PERK and EIF2A in post-mortem human PSP brain tissue vs. the effects of PERK activation and inhibition in a genetic and an environmental model of a PSP-like tauopathy.

In the Examples, further we present an in vivo study describing the in vivo effects of PERK activators, i.e. of the representative PERK activator CCT020312, on P301S mice on behavior and brain histology.

Example A. PERK Activation Mitigates Tau Pathology In Vitro

In Vitro Study on the State of PERK and EIF2A in Post-Mortem Human PSP Brain Tissue. Effects of PERK Activation Vs. Inhibition in a Genetic and an Environmental Model of a PSP-Like Tauopathy.

The unfolded protein response plays a key role in many neurodegenerative diseases. One of its key regulators, the Protein Kinase R-like Endoplasmic Reticulum Kinase (PERK), is genetically associated with Progressive Supranuclear Palsy (PSP). Here, we have found one of its main substrates, EIF2A, to be suppressed in the brains of PSP patients compared to controls without neurodegenerative diseases. We have created two cell culture models of PSP in differentiated human LUHMES neurons. One is based on lentiviral overexpression of wild type 4R-tau, the other on treatment with the complex I inhibitor annonacin which is associated with a PSP-like tauopathy in Guadeloupe. In these two models we have pharmacologically manipulated PERK with the activator CCT020312 and the inhibitor GSK2606414. PERK activation increased cell viability and reduced tau phosphorylation, tau conformational change and the amount of 4R-tau. These results were reproduced by lentivirus-mediated PERK overexpression. These findings demonstrate that activation of PERK may be a viable treatment strategy for PSP.

Introduction

Tauopathies are a heterogeneous group of neurodegenerative diseases defined by the common feature of intraneuronal or intracerebral aggregation of the microtubule associated protein tau. PSP is a prototypical sporadic tauopathy, characterized by predominant involvement of tau isoforms with 4 microtubule-binding repeats (4R-tau) rather than isoforms with 3 repeats (3R-tau). A genome wide association study (Hoglinger et al. 2011) confirmed the MAPT gene encoding tau protein and revealed three additional genes that influence the risk to develop PSP. One of these risk genes is EIF2AK3, encoding PERK.

PERK is an integral part of the unfolded protein response (UPR, FIG. 1A). Once induced by an overload of misfolded proteins in the endoplasmic reticulum (ER stress), PERK gets autophosphorylated and then phosphorylates EIF2A and NRF2. This, in turn, leads to global suppression of translation and changes in transcription via NRF2 activation and activating transcription factor 4 (ATF4), thereby protecting cells. The system may, however, also go into overdrive, activating apoptosis. Malfunction of the UPR results in severe developmental and functional deficits, including liver and kidney failure, diabetes mellitus and microcephaly. These can be observed in patients with Wolcott-Rallison syndrome, which is caused by mutations in EIF2AK3.

Apart from the genetic association (Hoglinger et al. 2011), there is some neuropathological evidence for a role of PERK in tauopathies, reviewed by Hetz et al. 2014. There is increased immunostaining for phosphorylated (i.e. activated) PERK in Alzheimer's disease pre-tangle neurons with tau aggregates in the hippocampus. UPR activation has also been reported in "Frontotemporal Dementia and Parkinsonism Linked to Chromosome 17" which is caused by MAPT mutations (FTLD-17-tau). In PSP, the UPR has been reported to be primarily activated in the pons and medulla and to a lesser extent in the hippocampus.

These findings have triggered a search for mechanisms of interaction between the UPR and tau.

PERK has been considered as a therapeutic target. Pharmacological PERK inhibition has been reported to halt disease progression in a prion protein based mouse model. Similarly, conditional PERK knockout improved synaptic plasticity and reduced defects in spatial memory in an Alzheimer's disease APP and PSEN1 mouse model. The rationale for using PERK inhibition as therapeutic approach in neurodegenerative diseases is that PERK may be chronically overactive in these diseases, leading to a long-term harmful suppression of translation. Nonetheless, long-term PERK inhibition also comes with serious consequences (diabetes mellitus, liver and renal impairment, amongst others), resembling symptoms of Wolcott-Rallison syndrome. Side effects in human xenograft tumor mice treated with a PERK inhibitor included severe diabetes mellitus within 14 days and a high level of mortality.

In contrast to PERK inhibition in the prior art, we have surprisingly found for the first time that activation of the UPR provides for a powerful protective mechanism in the context of several neurodegenerative diseases. The rationale is to harness the neurons' natural protective mechanism against protein aggregation. The PERK substrate NRF2 has been shown to increase cell survival following ER stress (Cullinan et al. 2003). The EIF2A/ATF4 pathway is also critical for stress-induced autophagy (B'Chir et al. 2013). Three compounds (salubrinal, guanabenz, phenazine), which prevent EIF2A dephosphorylation have been shown to protect against neurodegeneration in a TDP-43 model of amyotrophic lateral sclerosis (Vaccaro et al. 2013). Suppressing the UPR by Xpb1 inhibition worsened tau-induced apoptosis in a *drosophila* model (Loewen et al. 2010). Any therapy based on PERK will therefore need to activate the positive aspects of PERK, such as autophagy and NRF2 and ATF4 based neuroprotection, while avoiding overdrive to permanently suppress translation, or at least to cause long-term suppression of translation, and activate apoptosis.

Further Abbreviations

ATP (Adenosine triphosphate); MTT (Thiazolyl Blue Tetrazolium Blue); Pa=PA (PERK activator; i.e. CCT020312); Pi (PERK inhibitor GSK2606414); SEM (Standard error of the mean); Tg (Thapsigargin).

Materials and Methods

Cell Culture

Nunc™ Nunclon™ Delta 6-well (for protein and mRNA) or 48-well (for cell assays) plates (Thermo Fisher Scientific, Waltham, Mass., USA) were coated with 100 µg/ml poly-L-lysine (Sigma-Aldrich, St. Louis, Mo., USA) and 5 µg/ml fibronectin (Sigma-Aldrich). LUHMES (Lund Human Mesencephalic) cells, derived from female human embryonic ventral mesencephalic cells by conditional immortalization (Tet-off v-myc over-expression) were seeded out in a concentration of 130,000 cells/cm$^2$ to achieve a confluence of 50%. They were then differentiated for 8 days in a medium of DMEM/F12 (Sigma-Aldrich), 1 µg/ml tetracycline, 2 mg/ml GDNF and 490 µg/ml dbcAMP into post-mitotic neurons with a dopaminergic phenotype (Lotharius et al. 2005).

Pharmacological Treatments

Table 1 shows the substances used, their source, and their application. For all experiments with annonacin, the medium was replaced during the intoxication period with new medium containing glucose levels reduced to 250 µM, i.e. the physiological concentration in the human brain.

TABLE 1

Details of Substances used for Treatment

| Substance name | Source | Dissolving and dilution | Treatment concentration (unless indicated otherwise) | Treatment duration (unless indicated otherwise) |
|---|---|---|---|---|
| Annonacin | Extracted from *Annona Muricata* fruits by Pierre Champy, Univ. Paris-Sud, France | Dissolved in DMSO (AppliChem) to 1 mM, diluted further with medium | 25 nM | 48 h (days 8-10 post differentiation) |
| PERK activator (CCT020312) (Stockwell et al. 2012) | Merck Millipore, Billerica, MA, USA | Dissolved in DMSO to 10 mM, diluted further with medium | 200 nM | 48 h (days 8-10 post differentiation) |
| PERK inhibitor (GSK2606414) | Toronto Research Chemicals, North York, ON, Canada | Dissolved in DMSO to 10 mM, diluted further with medium | 300 nM | 48 h (days 8-10 post differentiation) |
| Thapsigargin | AppliChem, Darmstadt, Germany | Dissolved in DMSO to 10 mM, diluted further with medium | 30 nM | 48 h (days 8-10 post differentiation) |

Cloning of Transfer Vector Plasmids

Plasmids from various sources were applied as indicated in Table 2. The MAPT isoforms 2N3R and 2N4R and EIF2AK3 (the gene encoding mouse PERK) were amplified from the original plasmids by PCR with Q5® High-Fidelity DNA Polymerase (New England Biolabs, Ipswich, Mass., USA) using the primers as indicated in Table 3. MAPT 2N4R with the P301S mutation was removed directly from the original plasmid by enzymatic digestion with Xba1 and EcoR1. All MAPT genes were then inserted into the lentiviral vector plasmid FU-ΔZeo by digesting the vector with the restriction enzyme indicated in Table 3, followed by ligation with T4 ligase (New England Biolabs). EIF2AK3 was inserted using the Gibson method (Gibson et al. 2009) with the Gibson Assembly® Cloning Kit (New England Biolabs). The resulting ligated clones were transfected into 5-alpha competent *E. coli* (New England Biolabs) and grown on an ampicillin selective Luria Bertani (LB) agar (Sigma-Aldrich) plate. The next day, colonies were picked and amplified in LB medium (Sigma-Aldrich) for 8 hours with ampicillin for selection. The plasmid DNA was extracted using the NucleoBond Xtra Midi kit (Macherey Nagel, Düren, Germany) and sequenced for confirmation.

TABLE 2

Overview of Plasmids used for Cloning

| Gene Insert | Species | Full Plasmid Name | Reference |
|---|---|---|---|
| MAPT 2N3R | Human | pRK172/htau39 | |
| MAPT 2N4R | Human | pNG2 htau40 | |
| MAPT 2N4R-P301S | Human | TauP301S-d.PR4.172 | |
| EIF2AK3 | Mouse | PERK.WT.9E10.pCDNA.amp | Bouman et al. 2011 |
| n.a. | n.a. | FU-ΔZeo | Kuhn et al. 2010 |
| mCherry | Aequorea victoria | mCherry/FU-ΔZeo | |

TABLE 3

Primers and Restriction Enzymes used for Cloning of Vector Plasmids

| Original Plasmid | Forward Primer | Reverse Primer | Restriction Enzymes |
|---|---|---|---|
| pRK172/htau39 | GATCTCTAGAATCACAAACCCTGCTTGGCCAG | GATCGGATCCGATATACATATGGCTGAGCC | BamH1-HF, Xba1 |
| pNG2 htau40 | GATCTCTAGAATCACAAACCCTGCTTGGCCAG | GATCGGATCCGGAGATATACATATGGCTGAGCC | BamH1-HF, Xba1 |
| PERK.WT.9E10.pCDNA.amp | caggtcgactctagagGCGATGTCTGCACAAGGC | cgataagcttgatatcgGCCAGGCAGTGGCGTGTA | Gibson Assembly Mastermix |

Lentivirus Expression and Concentration

As described in Kuhn et al. 2010, lentiviruses were generated in HEK293T cells. The plasmids psPAX2, pCDNA3.1 (−)-VSV-G and the transfer vector FU-ΔZeo (generated as described above) were co-transfected using Lipofectamine 2000 and Opti MEM® (both by Life Technologies, Grand Island, N.Y., USA). 24 h post transfection the medium was replaced with DMEM+Pyruvate+GlutaMAX™ (Life Technologies)+10% fetal calf serum (Sigma-Aldrich)+1× essential amino acids (Life Technologies). 48 h after transfection the medium was ultra-centrifuged for 2 h at 22,000 rpm in a SW28 rotor (Beckman-Coulter, Brea, Calif., USA) and the supernatant was discarded. The concentrated lentiviral particle pellet was resuspended in TBS-5 (50 mM Tris, 130 mM NaCl, 10 mM KCl, 5 mM $MgCl_2$, 5% (w/v) BSA) for 4 h at 4° C. before aliquoting and storage at −80° C. until use.

Lentivirus Transduction

Concentrated lentiviral particles were titrated by transducing LUHMES cells with different dilutions at 6 hours after initiating differentiation. The lowest dilution at which at least 90% of cells expressed the transgene (as determined by immunohistochemistry of the cells fixed on day 2 post differentiation) was chosen for subsequent experiments. For these, concentrated lentiviral particles were again added into the medium on day 0, 6 hours after initiating differentiation.

Protein Extraction from Cells

Protein was extracted by scraping the cells from the culture plate with Mammalian Protein Extraction Reagent (M-PER, Thermo Fisher Scientific) and 1× cOmplete Protease Inhibitor Cocktail Tablets (Hoffmann-La Roche, Basel, Switzerland) and 1× PhosSTOP Phosphatase Inhibitor Cocktail Tablets (Hoffmann-La Roche). For pNRF2 blots, cells were extracted with 2% SDS tris-buffer instead of M-PER in order to obtain whole cell extracts and not to lose the nuclear fraction. The protein solution was frozen at −80° C., immediately after retrieval, for a minimum of two hours. The solution was then thawed on ice, vortexed, centrifuged at 5000 g for 15 min at 4° C. and the supernatant retrieved. Protein concentrations were determined using the BCA kit (Thermo Fisher Scientific) by heating the samples at 60° C. for 30 min and measuring the absorption on the NanoDrop 2000c Spectrophotometer (Thermo Fisher Scientific).

Human Brain Tissue

Fresh frozen tissue from the *gyrus frontalis* superior of seven PSP patients and three controls without psychiatric or neurodegenerative diseases was obtained from the Center for Neuropathology and Prion Research, University of Munich, as detailed in Table 4. Prior to death, all donors gave written informed consent according to the Declaration of Helsinki for the use of their brain tissue and medical records for research purposes. This work was approved by the local IRB and ethics committee.

TABLE 4

Overview of Human Tissue Samples used

| Case Number | Diagnosis | Age at death | Sex | Postmortem time (hours) |
|---|---|---|---|---|
| C1 | Control | 78 | Female | 8 |
| C2 | Control | 77 | Female | 10 |
| C3 | Control | 77 | Female | 20 |
| P1 | PSP | 62 | Female | 8.5 |
| P2 | PSP | 76 | Male | 12 |
| P3 | PSP | 76 | Female | 10 |
| P4 | PSP | 75 | Male | 12 |

TABLE 4-continued

Overview of Human Tissue Samples used

| Case Number | Diagnosis | Age at death | Sex | Postmortem time (hours) |
|---|---|---|---|---|
| P5 | PSP | 67 | Male | 40 |
| P6 | PSP | 69 | Male | 12 |
| P7 | PSP | 78 | Female | 30 |

Protein Extraction from Human Tissue

The relevant tissue was dissected from the fresh-frozen sample on dry ice and suspended in 750 μl of Tissue Protein Extraction Reagent (T-PER, Thermo Fisher Scientific) and 1× cOmplete Protease Inhibitor Cocktail Tablets (Hoffmann-La Roche) and 1× PhosSTOP Phosphatase Inhibitor Cocktail Tablets (Hoffmann-La Roche). The tissue piece was initially ground with a pestle inside a microcentrifuge tube on ice and then homogenized by sonification with Branson Sonifier 450 Analog (Branson, now Thermo Fisher Scientific) with 10×500 ms bursts at intensity level 3 on ice. The solution was then centrifuged and treated as described above for cells.

PERK Immunoprecipitation

200 μg of protein were diluted to equal concentrations with M-PER lysis buffer (Thermo Fisher Scientific) up to 270 μl. The PERK D11A8 antibody (Cell Signaling Technology, Beverly, Mass., USA) was added to a concentration of 1:100 and allowed to bind the antigen for one hour in a rotating 1.5 ml microcentrifuge tube. Then 30 μl of protein sepharose A beads (Sigma-Aldrich, 3 mg per ml) were added to each tube and left rotating overnight at 4° C. The tubes were then centrifuged at 10,000 g for 3 minutes and the supernatant was discarded. The beads were washed in M-PER three times. Each time the beads were centrifuged and the supernatant was extracted with a Hamilton Syringe (Hamilton, Bonaduz, Switzerland) and discarded. The beads were then mixed with 15 μl 1× Roti®-Load 1 (Carl Roth) and heated at 95° C. for 5 minutes. After another centrifugation step of 10,000 g for 1 minute the supernatant was loaded onto a gel with the Hamilton syringe and then blotted as described below.

Western Blotting

20 μg of protein (unless indicated otherwise) were adjusted to equal concentrations between samples by dilution with M-PER and subsequently heated at 95° C. for 5 minutes with Roti®-Load 1 (Carl Roth). SDS-PAGE was performed using Any kD™ Mini-PROTEAN® TGX™ Gels (BioRad, Berkeley, Calif., USA) in a tris-glycine running buffer. The protein was blotted onto PVDF membrane (BioRad) at 70 V for 65 minutes on ice. The membrane was blocked with 1× Roti®-Block solution (Carl Roth) for 1 h and then incubated at 4° C. overnight under gentle shaking with the primary antibody (see Table 5) in TBS with 5% BSA (Cell Signaling Technology) and 0.05% TWEEN (Sigma-Aldrich).

The membranes were then washed and incubated with the species specific HRP-bound secondary antibody (Vector Laboratories, Burlingame, Calif., USA) at 1:2500 in 1× Roti®-Block solution for 2 h, followed by further washing and exposure to Clarity Western ECL Substrate (BioRad) or, in the case of MC1 and 4R-tau, to Amersham™ ECL™ Prime (GE Healthcare). Chemiluminescence was detected with the Gel Doc™ XR System (BioRad) and analyzed with Image Lab™ software (BioRad), followed by graphical and statistical analysis with Prism 6 (GraphPad Software).

TABLE 5

Overview of antibodies used

| Antigen | Clone | Species | Concentration | Source |
|---|---|---|---|---|
| PERK | D11A8 | Rabbit | 1:1000 (WB) 1:100 (IP) | Cell Signaling Technology |
| pT980-PERK | 16F8 | Rabbit | 1:1000 | Cell Signaling Technology. Note: According to the manufacturer's information this antibody is only reactive to rat pPERK. However, in our experience it reacts to human pPERK more specifically than the Santa Cruz antibody if the protein concentration is sufficiently high. |
| p-Ser-396 PHF Tau | AD2 | Mouse | 1:2000 | BioRad |
| 4 repeat Tau | 1E1/A6 | Mouse | 1:333 | Merck Millipore |
| 3 repeat Tau | 8E6/C11 | Mouse | 1:1000 | Merck Millipore |
| p-Ser-202 Tau | CP13 | Mouse | 1:500 | Peter Davies, Albert Einstein College, NY, USA |
| Conformationally changed Tau | MC1 | Mouse | 1:333 | Peter Davies, Albert Einstein College, NY, USA |
| Total human tau | HT7 | Mouse | 1:1000 | Thermo Fisher Scientific |
| EIF2A | polyclonal | Rabbit | 1:1000 | Cell Signaling Technology |
| pS51-EIF2A | D9G8 | Rabbit | 1:1000 | Cell Signaling Technology |
| pS40-NRF2 | EP1809Y | Rabbit | 1:1000 | GeneTex (Irvine, CA, USA) |

Quantitative PCR

RNA from human tissue samples was extracted by grinding the tissue in liquid nitrogen to a powder and then dissolving it in the RA1 buffer supplied as part of the NucleoSpin® RNA (Macherey Nagel) RNA extraction kit+ 1% (v/v) 2-mercaptoethanol (Sigma-Aldrich). RNA from cells was extracted by scraping the cells from the culture plate with RA1 buffer+1% (v/v) 2-mercaptoethanol. The remaining extraction procedure was according to the manufacturer's instructions for the NucleoSpin® RNA kit. RNA concentrations were determined using the NanoDrop 2000c Spectrophotometer. The RNA was then transcribed into cDNA with the iScript™ cDNA Synthesis Kit (BioRad) using the manufacturer's instructions. Real-Time PCR was performed on the Applied Biosystems® StepOnePlus™ (Life Technologies) system using TaqMan® Universal Master Mix II and TaqMan® primers against total MAPT, MAPT 3R, MAPT 4R, EIF2A, EI2AK3 and ATF4. POL2A and PSCM1 served as reference targets as they were determined to be the most stably expressed across experimental conditions. The results were analyzed using the StepOne Plus software (Life Technologies) and Qbase software (Biogazelle) and were then graphically and statistically analyzed with Prism 6 (GraphPad Software). Absolute quantification was performed by creating a standard curve with plasmids containing either the 2N3R or the 2N4R spliced variant of MAPT (see Table 2). The absolute quantity was computed by deriving the relationship between CT values and absolute quantity with the StepOne Plus software.

ATP Assay

ATP assays were conducted using the ViaLight™ plus kit by Lonza according to the manufacturer's instructions. Luminescence was read with the FLUOstar Omega (BMG Labtech) platereader. The data was analyzed using the MARS Data Analysis Software (BMG Labtech) and Prism 6.

MTT Assay

Thiazolyl Blue Tetrazolium Blue (MTT) (Sigma Aldrich) was dissolved in sterile PBS to a concentration of 5 mg/ml. This stock solution was added to the cells in culture medium to achieve a final concentration of 0.5 mg/ml. The 48-well culture plate was then incubated at 37° C. for 1 h, the medium removed completely and frozen at −80° C. for 1 h. The plate was then thawed, 300 μl DMSO (AppliChem, Darmstadt, Germany) was added per well and the plate was shaken to ensure complete dissolution of the violet crystals. 100 μl from each well were transferred to a new 96-well plate and the absorbance was read with the FLUOstar Omega (BMG Labtech) platereader at a wavelength of 590 nM (reference wave length 630 nm). The data was analyzed using the MARS Data Analysis Software (BMG Labtech) and Prism 6.

Statistics

Prism 6 (GraphPad Software) was used for statistical calculations. Patients and controls were compared by t-tests with Sidak-Bonferroni correction. Results from cell culture experiments were generally compared by 2-way ANOVAs with Dunnett's post-hoc test, unless indicated otherwise. Biochemical assays with only treatment as a variable were compared by 1-way ANOVAs with Tukey's post-hoc test. Data are shown as mean±SEM. $P<0.05$ was considered significant.

Results

PERK is Upregulated, but EIF2A is Suppressed in PSP

We started by assessing the state of the UPR in human frontal cortex because of its consistent involvement in PSP. We were able to confirm the increased occurrence of phosphorylated PERK (pPERK) in PSP by Western blot (FIGS. 2A and B), which had previously been demonstrated by immunohistochemistry (Stutzbach et al. 2013). We also observed increased amounts of total PERK protein. The ratio of pPERK/PERK was not significantly increased. Levels of EIF2AK3 (PERK gene) mRNA expression (FIG. 2C) were not increased either. This suggests either increased translation or reduced proteolysis of PERK in PSP.

Interestingly, EIF2A protein, an important substrate of PERK kinase activity, was reduced, whereas EIF2A mRNA was unchanged in PSP (FIGS. 2A-C). There was also no increased phosphorylation of EIF2A (pEIF2A/EIF2A ratio), suggesting that the increased amount of pPERK does not actually result in higher EIF2A phosphorylation in PSP. Consistently, there was also no increase in ATF4 mRNA, the transcription of which is induced by pEIF2A.

In contrast to EIF2A, NRF2, a further substrate of PERK, had increased total protein levels and phosphorylated protein levels (pNRF2) in PSP, with no change in the pNRF2/NRF2 ratio.

UPR Changes in Two Models of Tauopathy

In an attempt to understand the alterations observed in human brains, we studied different interventions in differentiated human LUHMES neurons. LUHMES neurons exhibit properties very similar to primary human neurons and avoid the limitations associated with rodent and tumor neuronal cell lines.

Treatment with thapsigargin, an inhibitor of the sarco-/endoplasmic reticulum calcium ATPase (SERCA), which induces ER stress and activates the UPR (10), led to increased phosphorylation of both PERK and EIF2A protein (FIGS. 2D and E). The pPERK/PERK ratio was significantly increased ($p<0.5$). It also increased expression of EIF2AK3 and ATF4 mRNA (FIG. 2F), as would be expected from existing knowledge about the PERK-EIF2A-ATF4 axis (cf. FIG. 1A). This suggests that the UPR alterations observed in PSP are not a mere consequence of ongoing ER stress.

We then investigated the effect of an environmental model of tauopathy. Annonacin is a complex I inhibitor occurring in some fruit, including the soursop (*Annona muricata*). Its consumption has been linked to a PSP-like tauopathy on Guadeloupe. It reproduces hallmarks of a tauopathy in cultured neurons, including hyperphosphorylation and redistribution of tau from the axons to the cell body and eventual cell death (Escobar-Khondiker et al. 2007). When treating differentiated LUHMES neurons with 25 nM annonacin for 48 h, pPERK was increased and total PERK, pEIF2A and total EIF2A protein were reduced (FIGS. 2D and E). EIF2A and ATF4 mRNA were both upregulated (FIG. 2F). Thus, with the upregulation of pPERK and downregulation of pEIF2A and total EIF2A on the protein level, annonacin reproduced parts of the pattern seen in human PSP.

We then overexpressed wild-type tau using lentiviruses, as it had been previously described in rats where it induces slow and progressive neurodegeneration in vivo (Caillierez et al. 2013). We treated LUHMES cells with lentiviruses to express either wild-type 4R2N-tau, wild-type 3R2N-tau or the fluorescent control protein mCherry under control of the ubiquitin promoter. The 4R2N-tau encoding virus lead to an increase in expression of 4R-tau mRNA from a control-level of 80±10 to 5000±2000 copies/ng total mRNA; the 3R2N-tau virus led to an increase of 3R-tau mRNA from 1800±700 to 7600±300 copies/ng total mRNA; the specific increase of either 3R or 4R-tau by these viruses was confirmed by Western blotting (FIG. 8). None of the lentiviral models induced a significant increase in PERK or pPERK protein, suggesting that tau overload, by itself, is not sufficient to activate the UPR. However, 4R-tau (but not 3R-tau or mCherry) also suppressed EIF2A and pEIF2A at the protein level, as it was seen in PSP. As in PSP, none of the viruses changed EIF2AK3, EIF2A or ATF4 at the mRNA level (FIG. 2F).

Both annonacin and wild type 4R-tau overexpression mimicked PSP by down-regulation of EIF2A and pEIF2A at the protein level. However, none of these models mimicked the upregulation of PERK and pPERK, as seen in PSP. The latter might be a long-term compensatory mechanism to counteract the primary EIF2A downregulation and therefore not visible in the rather short-term cell culture models. Interestingly, we observed a discordant regulation of pEIF2A and ATF4 in PSP and the LV4R tau and annonacin models, suggesting that other regulatory influences on ATF4 mRNA do exist and that the UPR alterations observed in PSP are not a mere consequence of ongoing ER stress.

UPR Changes with Pharmacological Modulation

Specific pharmacological PERK inhibitors are available (Axten et al. 2012). There is also one pharmacological PERK activator, CCT020312 (Stockwell et al. 2012), which has been shown to increase EIF2A phosphorylation. Its molecular target was identified as PERK because siRNA-mediated knockdown of PERK and PERK$^{-/-}$ knockout mouse embryo fibroblasts abolished all effects of the drug and the other arms of the UPR remained unaffected (Stockwell et al. 2012).

In LUHMES neurons, we tested both the PERK inhibitor GSK2606414 and the PERK activator CCT020312 and identified non-toxic concentrations effectively modifying EIF2A phosphorylation (PERK activator: 200 nM; PERK inhibitor: 300 nM; FIGS. 3A-C). These concentrations were applied to all subsequent experiments.

We explored the effect of these pharmacological agents on phosphorylation of EIF2A and NRF2, two substrates of PERK kinase activity (FIG. 1A), in the annonacin and lentivirus based cell culture models of tauopathy, described above.

In the presence of annonacin (FIGS. 3D and F), the PERK activator increased only pNRF2 significantly, and the PERK inhibitor reduced pEIF2A levels significantly.

In the situation of lentiviral 3R or 4R-tau overexpression, the PERK activator did not increase pEIF2A (FIGS. 3E and G). However, the PERK activator significantly increased pNRF2 in 4R overexpressing cells. The PERK inhibitor only decreased pEIF2A but not pNRF2 in conditions of 4R-tau overexpression. There was no significant effect with lentiviral 3R-tau overexpression.

Pharmacological PERK Activation Protects Neurons in Both Models of Tauopathy

We continued to test the effect of PERK activation and inhibition on the viability of LUHMES neurons treated with annonacin or overexpressing 3R- or 4R-tau. Cell viability was determined with two biochemical assays: the MTT test, assessing mitochondrial reducing activity and measurement of the intracellular ATP concentration.

Annonacin caused a concentration-dependent decline in both MTT signal and ATP concentration (FIGS. 4A, B). Co-treatment with the PERK inhibitor did not significantly improve the MTT test, but slightly improved ATP concentrations at the single annonacin concentration of 12.5 nM. However, when treated with the PERK activator, there was a significant improvement in both MTT and ATP assay over a broad range of annonacin concentrations (FIGS. 4A, B).

In the lentiviral tau overexpression model, only the 4R-tau isoform, but not the 3R-isoform led to significant neurotoxicity compared to the control protein mCherry (FIGS. 4C, D). This 4R-specific toxicity was reduced significantly by co-administration of the PERK activator in both MTT and ATP assays. Interestingly, also the PERK inhibitor provided protection in the ATP assay, but to a lesser extent.

The protection by the PERK activator against annonacin and 4R-tau protein overexpression was also evident on morphological inspection of the cells. Annonacin reduced the density of the dendritic network (FIG. 4E) and led to the condensation of DNA to chromatin clumps (FIG. 4F). Lentiviral 4R-tau overexpression had similar effects. Counting the number of viable cells in each condition confirmed that the PERK activator mitigated these effects, i.e. the toxicity of both annonacin and 4R-tau overexpression. Cell counts of viable cells with intact nuclear and somatic morphology were counted in randomly selected 1300×1000 sized areas in 4 biological replicates each, confirming the protective effects of Pa.

PERK Activation Reduces Pathological Tau Conformation and Phosphorylation

We then evaluated the effect of the PERK activator on tau protein.

An early marker of tau pathology is the MC1 epitope. The antibody MC1 detects a pathological conformation of tau where two parts of the tau molecule separated by more than 300 amino acids come together and which is characteristic for paired helical filament tau (Jicha et al. 1997). We found annonacin, but not 4R- or 3R-tau overexpression, to increase the level of this pathological tau conformation. This effect was reversed by the PERK activator (FIG. 5A, B). This effect was also apparent on dot blots with non-denatured proteins.

Annonacin significantly increased phosphorylation of tau, as detected by antibodies CP13 (p-Ser-202-tau) (Ishizawa et al. 2003) and AD2 (p-Ser-396 and 404 tau) (Buee-Scherrer et al. 1996) (FIG. 5C-E). This effect was significantly reduced by the PERK activator. Total tau protein, which was identified with the HT7 antibody, was not altered by treatment with annonacin or the PERK activator (FIG. 5C, F).

In cells treated with 4R-tau overexpressing lentivirus, there was a significant increase in CP13 phosphorylated tau; this Ser-202 phosphorylation was also significantly reduced by the PERK activator (FIGS. 5G-J). Also AD2- and HT7-positive tau was increased upon 4R overexpression, however, this was not altered by treatment with the PERK activator.

PERK Activation Reduces the 4R-Tau Isoform Shift

We have observed annonacin to increase the level of 4R-tau, but not 3R-tau, on both the protein and mRNA level (FIGS. 6A-C), depending on the splicing factor SRSF2, making annonacin a suitable model for testing effects on tau alternative splicing.

Here, we tested if PERK activity could reverse the increase in 4R tau. Indeed, addition of the PERK activator reduced the amount of 4R-tau mRNA and protein again, thus almost reversing the effect of annonacin on the 3R/4R isoform balance. Subsequently, we tested if this effect of PERK is also mediated via the splicing factor SRSF2. We screened the splicing factors known to impact 3R/4R alternative splicing (Liu et al. 2008) and found annonacin to significantly increase only the splicing factor SRSF2. The PERK activator significantly reduced this effect (FIG. 6D), providing a rationale for the effect of PERK on tau isoform balance. In this, PERK appears to act at or upstream of the splicing factor SRSF2 to mitigate 4R-tau upregulation.

The Effects of the PERK Activator can be Reproduced by PERK Overexpression

Overexpression of wild type PERK results in its activation in the absence of activating signals. This is because levels of ectopic PERK exceed levels of available ER-resident chaperone binding immunoglobulin protein (BiP) and lead to EIF2A phosphorylation in the absence of ER stress. We thus created a lentivirus overexpressing wild type PERK in order to confirm the effects of the PERK activator with an independent method. The lentivirus results in a 3-fold overexpression of PERK, as shown by a representative Western blot for PERK and actin, when LUHMES cells are incubated for 8 days with PERK overexpressing lentivirus; quantification was performed on three biological replicates of Western blots: t-Test vs. untreated cells: ## $p<0.01$ vs. control. We found that PERK overexpression protects human dopaminergic neurons both from toxicity induced by annonacin (FIGS. 7A, B) or by 4R-tau overexpression (FIGS. 7C, D). PERK overexpression also reduced the 4R-tau mRNA levels increased by annonacin (FIG. 7E). This suggests that the effects observed with the PERK activator were indeed mediated by increased PERK activity and not by off-target effects.

Discussion

We have provided evidence for the potential usefulness of pharmacological PERK activation in the treatment of tauopathies such as PSP. We have used two separate models—one based on overexpression of wild-type tau and one based on the mitochondrial complex I inhibitor annonacin, which is epidemiologically linked to a PSP-like tauopathy and reproduces many features of PSP in vitro. In these models we have shown that PERK activation reduces phosphorylated tau, reduces tau with pathological conformational change, decreases 4R-tau isoforms and improves cell viability.

EIF2A is Suppressed and PERK Highly Expressed in PSP

We have shown that the amount of EIF2A protein is lower in the frontal cortex of PSP patients compared to controls (FIG. 1B). This suppression can be reproduced by 4R-tau overexpression in human neurons. This makes it likely that it is tau protein, and particularly its 4R isoforms, that mediates this suppression of EIF2A in PSP patients. The increased PERK expression in PSP patients may therefore be an attempt to overcome the effects of EIF2A suppression through a long-term negative feedback mechanism.

EIF2A is Suppressed in Our Tauopathy Models

Different models have shown very different and often conflicting results to the question of whether more or less UPR activity is beneficial in neurodegenerative diseases. Therefore, it is especially important to choose a model that reflects the atypical pattern of UPR activation seen in the original human disease. We have shown that tau overexpression in human neurons per se does not lead to UPR activation. Annonacin does, however, activate PERK while reducing EIF2A, a feature that resembles the state in human PSP. Overexpression of 4R-tau, and to a lesser extent 3R-tau, does not increase PERK activity significantly but still suppresses EIF2A. The increase in PERK observed in PSP patients' brains may take longer to develop than the short-term treatment periods in our models. Still, annonacin and 4R overexpression both appear to sufficiently model aspects of the human disease.

PERK Activation is Protective in Models of Tauopathy

In our models of tauopathy, we have seen much greater neuroprotective effects with the selective PERK activator CCT020312 than with the PERK inhibitor GSK2606414. The PERK activator molecule is presently unique in that it does not work by inducing ER stress, and instead selectively activates PERK signaling (Stockwell et al. 2012).

We have shown that this protective effect may be due to the predominant NRF2 response, and that in conjunction therewith, in the presence of increased amounts of 4R-tau (i.e. in PSP, 4R-tau overexpression and annonacin treatment) the EIF2A response is inhibited. In this condition, NRF2 gets preferentially activated by PERK (FIG. 1B). NRF2 is a transcription factor, which has been shown to support the survival of cells especially under conditions of oxidative stress. Any additional activation of the suppressed EIF2A response, sufficient to activate ATF4 mediated protective mechanisms without activating the apoptotic cascade, may also contribute.

Although, these results only show short-term effects in vitro, promising initial results could be observed from chronic pharmacological PERK activation in vivo.

The detrimental effects of UPR overactivation were only seen at CCT020312 doses in excess of 3 µM. Our finding is supported by several previous reports of UPR activity protecting cells from various forms of tauopathy and protein aggregation (Boyce et al. 2005; Loewen et al. 2010; Vaccaro et al. 2013).

Also, some previous publications using models not involving tau (such as the prion protein and APP and PSEN1 mouse models mentioned in the introduction) have reported significant protective effects by reducing PERK activity. It has been proposed (Scheper et al. 2013; Hetz et al. 2014) that any protective effect of PERK inhibition in these models may be due to the disinhibition of a harmful long-term suppression of translation and prevention of the pro-apoptotic effects of EIF2A. Especially the prion model used by Moreno et al. 2013 has a high level of EIF2A activity—in contrast to PSP and in cells with 4R-tau overexpression. We have shown that in conditions of 4R-tau overexpression, weakening the already suppressed EIF2A response further by pharmacological PERK inhibition does not lead to major improvements in cell viability.

PERK has Diverse Effects on Tau

We have identified several effects of PERK activation on tau, such as a reduction in phosphorylation at serine 202 and 396, reduction in the MC1-positive conformation and a reduction in 4R-tau via down-regulation of splicing factor SRSF2. Reports that tau colocalizes with PERK (Stutzbach et al. 2013) seem to support the idea of a direct interaction. Thus, PERK may play several significant roles in tauopathies mitigating cellular stress levels. Further studies are required to address the relative significance of the effects of PERK on tau directly compared to more general cellular stress protective effects.

Conclusion:

To summarize our findings (FIG. 1), we describe here that EIF2A is suppressed in human PSP and in two cell culture models of tauopathy. We also show that PERK activation is protective in these two models and that PERK activity can lead to the reduction in 4R isoform tau by SRSF2 down-regulation, reduced tau phosphorylation and reduced MC1-positive tau conformation change. Therefore, PERK activation may represent a new potential treatment strategy for PSP and related 4R-tauopathies.

Example B. PERK Activation Mitigates Tau Pathology In Vivo

In Vivo Study on the Effects of Compound CCT020312 as Representative PERK Activator on Behavioral Deficits and Brain Tau Pathology in P301S Tau Transgenic-Mice.

In addition to the prior cell culture work (see EXAMPLE A), suggesting efficacy of PERK activation to protect against neuronal death in cell culture models of tau pathology, here we further studied the PERK activator CCT020312 in transgenic mice with neuronal overexpression of a P301S-mutant human tau protein (Xu et al. 2014). We confirmed first evidence suggesting brain penetration, and thus cerebral target engagement upon peripheral administration, as well as safety and efficacy reducing cerebral levels of phosphorylated tau and in a memory and motor task after 6 weeks of daily i.p. administration of CCT020312. These findings demonstrate that chronic pharmacological activation of PERK can represent a new treatment strategy for tauopathies in vivo.

As indicated, tauopathies are a group of neurodegenerative diseases defined by intracerebral aggregation of the microtubule associated protein tau. One of the most widely accepted experimental animal models for tauopathies are mice with the P301S mutation (Xu et al. 2014). The mutation leads to the formation of tangles, tau phosphorylation and several behavioral hallmarks of tauopathies, such as memory and motor deficits.

One of the cellular mechanisms that show abnormality in tauopathies is the unfolded protein response. PERK is one of the key initiators of the unfolded protein response. Once induced by an overload of misfolded proteins in the endoplasmic reticulum (ER stress), PERK phosphorylates eukaryotic translation initiation factor 2-alpha (EIF2A) and nuclear factor erythroid 2-related factor 2 (NRF2) (FIG. 1A).

As stated, when PERK has been considered as a therapeutic target, pharmacological PERK inhibition has been reported to halt disease progression in a prion protein based mouse model, or in that conditional PERK knockout improved synaptic plasticity and reduced defects in spatial memory in an Alzheimer's disease APP and PSEN1 mouse model. But, as mentioned long-term PERK inhibition comes with serious consequences, like diabetes mellitus, liver and renal impairment, amongst others, resembling symptoms of Wolcott-Rallison syndrome. In contrast to PERK inhibition, here we propose to activate the UPR as a protective mechanism in the context of neurodegenerative diseases.

In the following study, we describe the in vivo effects of the PERK activator CCT020312 in wild type and P301S mice. Target engagement of the compound and effects on behavior, using the Morris Water Maze and the Rotarod Test, and on brain histology are shown.

Materials and Methods

Mice

All animal work was conducted either on CR57BL/6 mice, obtained from Charles River Laboratories, Wilmington, Mass., USA, or on homozygous transgenic mice overexpressing human tau with the P301S mutation on a C57BL/6 background, originally developed by Michel Goedert (Xu et al. 2014), obtained by own breeding. Animals were kept at 23±1° C. under standard 12 h light-dark cycle with free access to food and water. They were handled according to the EU Council Directive 2010/63/EU, the Guide for the Care and Use of Laboratory Animals (National Research Council 2011) and the guidelines of the local institutional committee. The experiments were authorized by the local authority "Regierung von Oberbayern" under application number 55.2-1-54-2532-165-13.

Administration of the PERK Activator (PA)

5 mg of the PA compound CCT020312 (EMD Millipore, Billerica, Mass., USA) was first dissolved in 100 µl sterile DMSO (AppliChem, Darmstadt, Germany) and then diluted in sterile saline (B. Braun Medical, Melsungen, Germany) to achieve a stock solution of 200 mg/ml.

For the initial short-term single-dose target-engagement trial, wild type mice were treated on three consecutive days with either 2 mg/kg of CCT020312 or saline of the equivalent volume by intraperitoneal injection. They were sacrificed by cervical dislocation four hours after the last injection.

For the short-term ascending-dose target-engagement trial, wild type mice at 15 weeks of age were treated on three consecutive days with once daily intraperitoneal (i.p.) injections of either 1, 2, or 5 mg/kg of CCT020312 or equivalent volumes of saline.

For the long-term single-dose target-engagement trial, wild type mice (n=3) at 9 weeks of age were treated for 6 weeks with once daily i.p. injections of either 2 mg/kg of CCT020312 or equivalent volumes of saline.

Mice were sacrificed by cervical dislocation twelve hours after the last injection. Their brains were frozen on dry ice and stored at −80° C. for Western blot analysis.

For the efficacy trial in the early disease stage (Xu et al. 2014), P301S mice (n=8 per group) and wild type littermates (n=9 per group) received once daily i.p. injections of 2 mg/kg CCT020312 or equivalent volumes of saline from 9 to 14 weeks of age; they were analyzed with the Morris Water Maze in the 15$^{th}$ week of age.

For the efficacy trial in the late disease stage (Xu et al. 2014), P301S mice and wild type littermates received once daily i.p. injections of 2 mg/kg CCT020312 or saline from 17 to 22 weeks of age (n=12 for CCT020312 treated P301S mice, n=9 for other groups); they were analyzed with the Rotarod test in the 23$^{rd}$ week of age.

Morris Water Maze

To analyze spatial learning and memory, the Morris water maze test was performed at 15 weeks of age (n=8 per group) in a cylindrical water basin (diameter 120 cm) filled with water with a depth of 31 cm. The water was dyed with tasteless and odorless non-dairy creamer. A platform (diameter 12 cm) was hidden 1 cm below the water surface. Four distinct large signs were placed on the four walls of the room as visual cues. The whole test procedure consisted of 3 days pre-training to familiarize the mice with the test, and 3 days training as described in Xu et al. 2014. During the pre-training period, mice had 6 test runs with a visible platform on the first day, followed by 6 runs each day on day 2 and 3 with a hidden platform. Each run lasted a maximum of 2 min. Mice that did not find the platform were gently guided to the platform and allowed to stay on it for at least 10 sec. During pre-training, the position of the platform varied from day to day. During the training period, mice had one trial per day to find the hidden platform in a fixed position within 2 min on three consecutive days. Twenty-four hours after the training, a probe trial was done without the presence of the hidden platform, during which the mice were allowed to explore the maze freely within 2 min. Tracks of training and probe trial were recorded with the computerized Viewer2 system (Biobserve, Mannheim, Germany).

Rotarod Test

To monitor the balancing ability at 23 weeks of age (n=12 for CCT020312 treated P301S mice, n=9 for other groups), each mouse was placed on a rod with 30 mm diameter rotating at a constant speed of 10 rpm for a maximum of 2 min, as described (Xu et al. 2014). Mice were given six trials on one day to familiarize themselves with the task. On the following day, they were given six chances to stay on the rotating rod, recording their latency to fall (TSE Systems, Bad Homburg, Germany). The three best performances were used for the statistical analysis.

Mouse Brain Tissue

Twelve hours after the last injection, animals were anesthetized by i.p. injections of pentobarbital at (100 mg/kg) and transcardially perfused with 0.1 M phosphate buffer for 2 min, then fixed for 10 min with 4% paraformaldehyde. Post-fixation of the brain was done in 4% paraformaldehyde at 4° C. for 48 h. Their brains were prepared for histological analysis, as described (Xu et al. 2014). For the immunoblot analysis in P301S mice and wild type mice were sacrificed by cervical dislocation, their brains were frozen on dry ice and stored at −80° C. for Western blot analysis.

Protein Extraction

Frontal cortex tissue was dissected from the fresh-frozen sample on dry ice and suspended in 750 μl of T-PER Tissue Protein Extraction Reagent (Thermo Fisher Scientific) and 1× cOmplete Protease Inhibitor Cocktail Tablets (Hoffmann-La Roche) and 1× PhosSTOP Phosphatase Inhibitor Cocktail Tablets (Hoffmann-La Roche). The tissue piece was initially ground with a pestle inside a microcentrifuge tube on ice and then homogenized by sonification with Branson Sonifier 450 Analog (Branson, now Thermo Fisher Scientific) with 10×500 ms bursts at intensity level 3 on ice. The solution was then centrifuged at 5000 g for 15 minutes at 4° C. and the supernatant retrieved. Protein concentrations were determined using the BCA kit (Thermo Fisher Scientific) by heating the samples at 60° C. for 30 minutes and measuring the absorption on the NanoDrop 2000c spectrophotometer (Thermo Fisher Scientific).

Western Blotting

20 μg of protein (200 μg for pPERK blots) were adjusted to equal concentrations between samples by dilution with M-PER and subsequently heated at 95° C. for 5 minutes with Roti®-Load 1 (Carl Roth). SDS-PAGE was performed using Any kD™ Mini-PROTEAN® TGX™ Gels (BioRad, Berkeley, Calif., USA) in a tris-glycine running buffer. The protein was blotted onto PVDF membrane (BioRad) at 70 V for 65 minutes whilst being cooled with ice. The membrane was blocked with 1× Roti®-Block solution (Carl Roth) for 1 h and then incubated at 4° C. overnight under gentle shaking with the primary antibody (see Table 6) in TBS with 5% BSA (Cell Signaling Technology) and 0.05% TWEEN (Sigma-Aldrich). The membranes were then washed and incubated with the species specific HRP-bound secondary antibody (Vector Laboratories, Burlingame, Calif., USA) at 1:2500 in 1× Roti®-Block solution for 2 h, followed by further washing and exposure to Clarity Western ECL Substrate (BioRad) or, in the case of MC1, to Amersham™ ECL™ Prime (GE Healthcare). Chemiluminescence was detected with the Gel Doc™ XR System (BioRad) and analyzed with the Image Lab™ software (BioRad), followed by graphical and statistical analysis with Prism 6 (GraphPad Software).

TABLE 6

Overview of antibodies used

| Antigen | Clone | Species | Concentration | Source |
|---|---|---|---|---|
| PERK | D11A8 | Rabbit | 1:1000 (WB) | Cell Signaling Technology |
| pT980-PERK | 16F8 | Rabbit | 1:1000 | Cell Signaling Technology. Note: According to the manufacturer's |

TABLE 6-continued

Overview of antibodies used

| Antigen | Clone | Species | Concentration | Source |
|---|---|---|---|---|
| | | | | information this antibody is only reactive to rat pPERK. However, in our experience it reacts to human pPERK more specifically than the Santa Cruz antibody if the protein concentration is sufficiently high. |
| p-Ser-202 Tau | CP13 | Mouse | 1:1000 (WB) 1:500 (IH) | Peter Davies, Albert Einstein College, NY, USA |
| Conformationally changed Tau | MC1 | Mouse | 1:1000 (WB) 1:500 (IH) | Peter Davies, Albert Einstein College, NY, USA |
| Paired Helical Filament-tau | AT180 | Mouse | 1:1000 (WB) 1:500 (IH) | Thermo Fisher Scientific (Waltham, Massachusetts, USA) |
| EIF2A | polyclonal | Rabbit | 1:1000 | Cell Signaling Technology |
| pS51-EIF2A | D9G8 | Rabbit | 1:1000 | Cell Signaling Technology |
| pS40-NRF2 | EP1809Y | Rabbit | 1:1000 | GeneTex (Irvine, CA, USA) |
| NRF2 | EP1808Y | Rabbit | 1:1000 | Abcam (Cambridge, UK) |

Immunohistochemistry

Fixed brains (n=6 per group) were cut into 30 µm-thickness of coronal sections with a cryomicrotome (CM3050 S, Leica). Free floating sections were immunostained with AT180 (made in mouse, 1:500, Thermo Fisher Scientific, Waltham, Mass.), CP13, MC1 (both generous gifts from Professor Peter Davies, Department of Pathology, Albert Einstein College of Medicine) antibodies, separately raised against paired helical filament (PHF)-tau phosphorylated at threonine 231, phosphorylated tau at serine 202 and conformationally changed tau respectively. The immunoreactivity was revealed by biotinylated secondary antibodies (donkey anti-mouse, IgG (H+L), 1:1000, Jackson ImmunoResearch Europe, Suffolk, UK) and 3,3'-diaminobenzidine (SERVA Electrophoresis, Heidelberg, Germany). The results were repeated by six biological repeats per group.

Results

Model Characterization:

We performed an initial study if the P301S tau transgenic mice would be a good model to study the therapeutic effects of a PERK activator. The protein levels of PERK, phosphorylated PERK (pPERK), EIF2A, and phosphorylated EIF2A (pEIF2A) in brains of P301S tau mice at ages of 2 and 6 months to wild type CR57BL/6 mouse at 6 months of age were compared (FIG. 9A). We found PERK upregulated and EIF2A downregulated in P301S mice at both ages compared to the wild type CR57BL/6 mouse. pPERK, however, only became upregulated at 6 months of age in P301S mice, suggesting that this might be a long-term compensatory process. Despite this increase in PERK and pPERK, there was no concomitant increase in pEIF2A. The results observed in aged P301S mice largely reproduce the findings obtained in PSP patients' brains (FIG. 1B).

Target Engagement:

We next analyzed target engagement, i.e. if peripheral (intraperitoneal) administration of CCT020312 would lead to PERK activation in the brain of mice.

Therefore, we injected wild type mice once daily for three consecutive days with 2 mg/kg CCT020312 or saline (control) and analyzed the cerebral protein levels of pEIF2A, which is generated by EIF2A by the PERK kinase activity. We found a marked increase in EIF2A phosphorylation in whole brain extracts of the treated mice compared with those mice treated with saline only (see FIG. 10A), suggesting that peripheral administration of CCT020312 engages its cerebral molecular target PERK.

To look for a dose-response relationship, we injected wild type mice once daily for three consecutive days with 1, 2, or 5 mg/kg CCT020312 or saline (control) and analyzed the cerebral protein levels of phosphorylated PERK and phosphorylated NRF2, which is generated by the PERK kinase activity. We found a marked increase in PERK phosphorylation in whole brain extracts of the treated mice compared with those mice treated with saline only (FIG. 10B), suggesting that peripheral administration of CCT020312 engages its cerebral molecular target PERK. Further, we found a dose-dependent increase on the level of pNRF2 without significant change in total NRF2, confirming a dose-dependent activation of the PERK-NRF2 pathway in vivo (FIG. 10B).

To look for target-engagement in a longer-term treatment paradigm, we treated young wild type and P301S tau mice, starting from week 9 of age, either with saline (carrier solution, as a control) or CCT020312 (2 mg/kg once daily) for a duration of 6 weeks. We analyzed the activated PERK (phosphorylated PERK/pPERK), total PERK, pNRF2 and NRF2 in the brain of wild type mouse with a long-term intraperitoneal injection of CCT020312 (2 mg/kg, once daily for 6 weeks). Mice treated with CCT020312 have an increase of pPERK in the brain while no obvious change in the total PERK level (FIG. 10C). We also found a significant increase of pNRF2 level without significant change of total NRF2 levels in the treated mouse brains, suggesting 6 weeks of CCT020312 administration is sufficient to activate the PERK-NRF2 pathway and upregulate the level of both activated PERK and NRF2 (FIG. 10C).

First Evidence Suggesting Safety and Efficacy In Vivo:

We next analyzed, if peripheral administration of CCT020312 would be safe and show first signs of therapeutic efficacy.

Young wild type and P301S tau mice were treated either with saline (carrier solution, as a control) or with 2 mg/kg of CCT020312 for a duration of 6 weeks, starting from week 8 of age. No CCT020312-treated mouse of the wild type group (N=8) and of the P301S tau group (N=8) died during the treatment period or showed any obvious signs of sickness.

The Morris water maze test was used to monitor visuospatial memory as behavioral deficit arising from hippocampal dysfunction in P301S mice (Xu et al. 2014). In brief, this test monitors the improvement of mice over three consecutive days of testing in the latency to find a hidden platform in a water basin. We observed that wild type mice show a gradual shortening in latency over the three training days (FIG. 11A). P301S tau mice, however, exhibited less shortening in latency, i.e. less learning capacity, which was improved by treatment with the PERK activator. Specifically, on the third day of training (FIG. 11B), wild type mice had improved their latency to find the platform by more than 50% compared to the first day, on average; treatment with CCT020312 did not significantly affect the latency in wild type mice; P301S tau mice had improved their latency to find the platform only by about 20% (P<0.05 vs. all other groups); treatment with CCT020312 significantly improved the latency in P301S tau mice (P<0.05).

Additionally, we tested the effectiveness of PERK activation in aged wild type and P301S transgenic mice at 23 weeks of age (after 6 weeks of once daily treatment with 2 mg/kg of CCT020312 or saline) to improve their locomotor skills using a Rotarod test. Again, no saline-treated wild type (n=9) and P301S tau mouse (n=9) and no CCT020312-treated wild type (n=9) and P301S tau mouse (n=12) died during the treatment period or showed any obvious signs of sickness. In comparison to saline-treated wild type mice, saline-treated P301S transgenic mice had a significantly shortened latency to fall off the rotating rod. This deficit was significantly improved by CCT020312 treatment. In the Rotarod test, evaluating the balancing performance, saline-treated P301S mice performed significantly worse compared to all other groups. PA-treated P301S mice showed a significantly increased performance compared to saline-treated P301S mice (data not shown).

After sacrificing the mice at 23 weeks of age, we analyzed the mouse brains with three different tau antibodies by immunoblot and immunohistochemistry. A decrease of MC1-, AT180- and CP13-immunoreactivity was found in the CCT020312-treated compared to saline-treated P301S transgenic mouse brains revealed by immunoblots (FIG. 12).

A decrease in AT180-immunoreactivity was observed in the hippocampal region of in the CCT020312-treated compared to saline-treated P301S transgenic mouse brains in the histological analysis (FIG. 13). These results suggest a decrease of pathogenic tau species in vivo by activation PERK.

Discussion

EIF2A is Suppressed and PERK Highly Expressed in PSP and P301S Mice

As we have shown, EIF2A is expressed at lower levels and is less phosphorylated in the frontal cortex of PSP patients compared to controls. This suppression can be reproduced in P301S tau mice. This makes it likely that it is tau protein, especially its 4R isoform that mediates this suppression of EIF2A in PSP patients. One potential interpretation is therefore that the increased PERK expression in PSP patients is an attempt by the cells to overcome the effects of EIF2A suppression through a long-term negative feedback mechanism that takes place over months—as we have demonstrated in untreated P301S tau mice.

PERK Activator CCT020312 is Active In Vivo and Appears to Penetrate the Brain

We have shown that treating mice with the PERK activator CCT020312 intraperitoneally leads to an increased level of phosphorylated EIF2A in the brain. This suggests that the drug enters the brain and increases PERK activity in the brain with the result of increasing EIF2A phosphorylation and NRF2 phosphorylation.

PERK Activation Leads to Improved Spatial Memory Function in Tauopathy Mice

We have demonstrated that once daily intraperitoneal administration of the PERK activator CCT020312 improves the performance on a spatial memory task of young P301S mice and on a locomotor task of aged P301S mice, almost to those levels seen in wild type mice. These behavioral improvements were paralleled by reduction in pathological tau species in the brains of P301S transgenic mice, as evidenced both by immunoblot and immunohistochemistry. This suggests that on a functional level, PERK activation mitigates the effects of tauopathy in vivo.

D. REFERENCES

Axten, J. M., et al. (2012). *J Med Chem* 55(16): 7193-207.
B'Chir, W., et al. (2013). *Nucleic Acids Res* 41(16): 7683-99.
Bouman, L., et al. (2011). *Cell Death Differ* 18(5): 769-82.
Boyce, M., et al. (2005). *Science* 307(5711): 935-9.
Boxer, et al. (2014). *Lancet Neurol.* 13(7): 676-85. doi: 10.1016/S1474-4422(14)70088-2.
Bruch, J, et al. (2015). *J Neuropathol Exp Neurol.* 74(8): 850-7.
Buee-Scherrer, V., et al. (1996). *Brain Res Mol Brain Res* 39(1-2): 79-88.
Caillierez, R., et al. (2013). *Mol Ther* 21(7): 1358-68.
Cullinan, S. B., et al. (2003). *Mol Cell Biol* 23(20): 7198-209.
Chung, et al. (2013). WO 2013/192165.
Escobar-Khondiker, M., et al. (2007). *J Neurosci* 27(29): 7827-37.
Gani, A. R., et al. (2015). *Arch Biochem Biophys* 568: 8-15.
Gibson, D. G., et al. (2009). *Nat Methods* 6(5): 343-5.
Hetz, C., et al. (2014). *Nat Rev Neurosci* 15(4): 233-49.
Hoglinger, G. U., et al. (2011). *Nat Genet* 43(7): 699-705.
Ishizawa, T., et al. (2003). *J Neuropathol Exp Neurol* 62(4): 389-97.
Jicha, G. A., et al. (1997). *J Neurosci Res* 48(2): 128-32.
Kuhn, P. H., et al. (2010). *EMBO J* 29(17): 3020-32.
Lee do, Y., et al. (2010). *PLoS One* 5(5): e10489.
Liu, F., et al. (2008). *Mol Neurodegener* 3: 8.
Loewen, C. A., et al. (2010). *PLoS One* 5(9).
Lotharius, J., et al. (2005). *J Neurosci* 25(27): 6329-42.
Ma, T., et al. (2013). *Nat Neurosci* 16(9): 1299-305.
Moon, H. S., et al. (2015). *Mol Carcinog*.
Moreno, J. A., et al. (2013). *Sci Transl Med* 5(206): 206ra138.
Ozasa, R., et al. (2013). *Cell Struct Funct* 38(2): 183-95.
Poewe, W., et al. (2015). *Mov Disord*.
Pytel, D., et al. (2014). *J Biomol Screen* 19(7): 1024-34.
Scheper, W., et al. (2013). *Sci Transl Med* 5(206): 206fs37.
Scheper, W., et al. (2015). *Acta Neuropathol*.
Stockwell, S. R., et al. (2012). *PLoS One* 7(1): e28568.
Stutzbach, L. D., et al. (2013). *Acta Neuropathol Commun* 1:31.
Tolosa, et al. (2014). *Mov Disord.* 29(4): 470-8. doi: 10.1002/mds.25824
Vaccaro, A., et al. (2013). *Neurobiol Dis* 55: 64-75.
van der Harg, J. M., et al. (2014). *Cell Death Dis* 5: e1393.
Win, S., et al. (2015). *J Hepatol* 62(6): 1367-74.
Wu, H. L., et al. (2009). *Cardiovasc Res* 81(1): 148-58.
Xie, W., et al. (2015). *PLoS One* 10(3): e0119738.
Xu, H., et al. (2014). *Neuropathol Appl Neurobiol* 40(7): 833-43.
Yan, Y., et al. (2010). *BMC Cancer* 10: 445.
Yang, L., et al. (2013). *J Biol Chem* 288(19): 13631-8.
Zhu, Y., et al. (2008). *J Neurosci* 28(9): 2168-78.

The invention claimed is:

1. A compound selected from the group consisting of: a direct or indirect PERK (protein kinase R-like endoplasmic reticulum kinase) activator, a prodrug thereof, a derivative thereof, and a pharmaceutically acceptable salt of any thereof, wherein the compound is 6-bromo-3-[5-(4-bromo-phenyl)-1-(3-diethylamino-propionyl)-4,5-dihydro-1H-pyrazol-3-yl]-4-phenyl-1H-quinolin-2-one (PERK activator CCT020312) and is used in the treatment of a tau-mediated neurodegenerative disease or a tau-mediated neurodegenerative pathological condition.

2. The compound of claim 1 that is used in the treatment of a neurodegenerative disease or a neurodegenerative pathological condition associated with abnormal phosphorylation, pathological conformational change, aggregation and accumulation in the somatodendritic compartment of the axonal microtubule-associated protein tau.

3. The compound of claim 2, wherein the compound is used in the treatment of a tauopathy or a tau aggregation.

4. The compound of claim 1, wherein the compound is functionally characterized as a compound that stimulates the kinase activity of PERK protein or as a compound for use in method to stimulate the kinase activity of PERK protein.

5. The compound of claim 1, wherein the neurodegenerative disease is at least one tauopathy or a neurodegenerative pathological condition associated with at least one hallmark of a tauopathy.

6. The compound of claim 5 wherein the at least one tauopathy is selected from the group consisting of 3R-tauopathy, 4R-tauopathy, and mixed 3R-/4R-tauopathy.

7. The compound of claim 5 wherein the tauopathy is a predominant or a concomitant pathology.

8. The compound of claim 5, wherein the at least one tauopathy is a form of 3R-tauopathy, 4R-tauopathy, or mixed 3R-/4R-tauopathy, and that is associated with a disease selected from the group consisting of:
  i. diseases where tauopathy is a predominant pathology, wherein the disease is selected from the group consisting of Progressive Supranuclear Palsy (PSP), Argyrophilic Grain Disease (AGD), Corticobasal Degeneration (CBD), Frontotemporal lobar degeneration with tau aggregation (FTLD-tau; sporadic or caused by MAPT mutations), Pick's disease (PiD), Tangle-predominant dementia, Guadeloupe-Parkinson Dementia Complex, Guam-Parkinson Dementia Complex (Lytico-Bodig disease), Dementia pugilistica (chronic traumatic encephalopathy), and Progressive subcortical gliosis; and
  ii. diseases where tauopathy is a characteristic concomitant co-pathology, wherein the disease is selected from the group consisting of Alzheimer's disease (AD), Huntington's disease (HD), Parkinson's disease (PD), Multiple System Atrophy (MSA), Motor neuron disease (MND) with neurofibrillary tangles, Hallervorden-Spatz disease (HSD), Creutzfeldt-Jakob disease (CJD), Gerstmann-Straussler-Scheinker Disease, Niemann-Pick Disease Type C, Lead encephalopathy, Myotonic dystrophy, Prion protein cerebral amyloid angiopathy, Postencephalitic parkinsonism, Subacute sclerosing panencephalitis (SSPE), Tuberous sclerosis, and Down's syndrome.

9. The compound of claim 5, wherein the at least one tauopathy is a form of 3R-tauopathy, 4R-tauopathy, or mixed 3R-/4R-tauopathy, and that is associated with a disease selected from the group consisting of Progressive Supranuclear Palsy (PSP), Corticobasal Degeneration (CBD), Argyrophilic Grain Disease (AGD), Pick's disease (PiD), Frontotemporal lobar degeneration with tau aggregation (FTLD-tau; sporadic or caused by MAPT mutations), Tangle-predominant dementia, Guadeloupe-Parkinson Dementia Complex, Guam-Parkinson Dementia Complex (Lytico-Bodig disease), Dementia pugilistica (chronic traumatic encephalopathy), Progressive subcortical gliosis, and any combination thereof.

10. A compound acting as a direct or indirect PERK activator, wherein the compound is 6-bromo-3-[5-(4-bromo-phenyl)-1-(3-diethylamino-propionyl)-4,5-dihydro-1H-pyrazol-3-yl]-4-phenyl-1H-quinolin-2-one (PERK activator CCT020312), a prodrug thereof, a derivative thereof, and a pharmaceutically acceptable salt of any thereof, wherein the compound acts as an activator of eukaryotic translation initiation factor 2-alpha kinase 3 (EIF2AK3/PERK).

11. The compound of claim 10 which increases at least one of the phosphorylation of EIF2A or NRF2.

12. A pharmaceutical composition comprising:
  a) a compound selected from the group consisting of: a direct or indirect PERK activator, a prodrug thereof, a derivative thereof, and a pharmaceutically acceptable salt of any thereof, wherein the compound is 6-bromo-3-[5-(4-bromo-phenyl)-1-(3-diethylamino-propionyl)-4,5-dihydro-1H-pyrazol-3-yl]-4-phenyl-1H-quinolin-2-one (PERK activator CCT020312), and
  b) at least one pharmaceutically acceptable component selected from the group consisting of excipients, additives, and auxiliaries.

13. The pharmaceutical composition of claim 12 used in the treatment or prophylaxis of a tau-mediated neurodegenerative disease or of a tau-mediated neurodegenerative pathological condition.

14. The pharmaceutical composition of claim 13 used in the treatment or prophylaxis of a disease selected from the group consisting of: Progressive Supranuclear Palsy (PSP), Corticobasal Degeneration (CBD), Argyrophilic Grain Disease (AGD), Pick's disease (PiD), Frontotemporal lobar degeneration with tau aggregation (FTLD-tau; sporadic or caused by MAPT mutations), Tangle-predominant dementia, Guadeloupe-Parkinson Dementia Complex, Guam-Parkinson Dementia Complex (Lytico-Bodig disease), Dementia pugilistica (chronic traumatic encephalopathy), Progressive subcortical gliosis, and any combination thereof.

* * * * *